United States Patent [19]

Noyori et al.

[11] Patent Number: 4,766,147

[45] Date of Patent: Aug. 23, 1988

[54] NOVEL 5-MEMBERED CYCLIC COMPOUNDS, PROCESS FOR PRODUCTION THEREOF, AND PHARMACEUTICAL USE THEREOF

[75] Inventors: Ryoji Noyori, Aichi; Masanori Fukushima, Nagoya; Seizi Kurozumi, Kokubunji; Satoshi Sugiura, Hino, all of Japan

[73] Assignee: Teijin Limited, Osaka, Japan

[21] Appl. No.: 823,146

[22] Filed: Jan. 29, 1986

Related U.S. Application Data

[63] Continuation of Ser. No. 534,256, Sep. 21, 1983.

[30] Foreign Application Priority Data

Oct. 7, 1982 [JP] Japan .................................. 57-175267
Oct. 7, 1982 [JP] Japan .................................. 57-175268
Feb. 14, 1983 [JP] Japan .................................. 58-21617
Mar. 10, 1983 [JP] Japan .................................. 58-38190

[51] Int. Cl.$^4$ .................. C07C 177/00; A61K 31/557
[52] U.S. Cl. ...................................... 514/530; 560/53; 560/118; 560/121; 562/463; 562/500; 562/503; 514/573

[58] Field of Search ..................... 562/430.3, 463, 500, 562/503; 560/53, 118, 121; 514/530, 573

[56] References Cited

U.S. PATENT DOCUMENTS 4,099,014 7/1978 Peterson ................................. 560/53
4,560,703 12/1985 Fukushima ......................... 514/530

FOREIGN PATENT DOCUMENTS 79733 5/1983 European Pat. Off. ............ 560/121

OTHER PUBLICATIONS

Bohlmann, Phytochemistry, 21, 125 (1982) abstract only.

Primary Examiner—Robert Gersil
Attorney, Agent, or Firm—Sherman and Shalloway

[57] ABSTRACT

Novel 5-alkylidene-4-substituted-2-cyclopentenones and 5-(1-hydroxy-aliphatic hydrocarbon)-4-substituted-2-cyclopentenones.

These novel cyclopentenones and 5-alkylidene-3-hydroxy-4-substituted cyclopentanones have a pharmaceutical activity for treatment of tumors.

5 Claims, No Drawings

NOVEL 5-MEMBERED CYCLIC COMPOUNDS, PROCESS FOR PRODUCTION THEREOF, AND PHARMACEUTICAL USE THEREOF

This application is a continuation of application Ser. No. 534,256, filed Sept. 21, 1983.

This invention relates to novel 5-membered cyclic compounds, a process for production thereof, and a pharmaceutical use thereof.

Prostaglandin (PG) is a living body regulating substance which is involved in various biological reactions such as contraction of smooth muscles, lowering of blood pressures and inhibition of platelet aggregation. It has been anticipated that prostaglandin as a living body regulating substance affects proliferation of cells. Santoro et al. reported in Cancer. Res. 37, 3774 (1977) that PGE series inhibit growth of tumors of B16 melanoma cell in vivo. W. A. Turner et al. reported that PGA series inhibit tumor cell proliferation and induce differentiation as a result of experiments in vitro using B16 melanoma cell and mouse neuroblastoma [Prostaglandins and Cancer: First International Conference, pages 365–368 (1982)].

Honn et al. reported a possibility of using PGA series as antitumor agents in view of the fact that PGA series strongly inhibit synthesis of DNA [Biochem. Biophys. Res. Commun. 87, 795 (1979)].

M. Fukushima et al. examined the effect of $PGD_2$ to inhibit proliferation of mouse leukemia cell L1210 and human leukemia cell lines, and reported that $IC_{50}$ of $PGD_2$ on L1210 cell is 2.4 micrograms/ml [Biochem. Biophys. Res. Commn., 105, 956 (1982)].

It is an object of this invention to provide novel 5-membered cyclic compounds.

Another object of this invention is to provide novel 5-membered cyclic compounds which have a 5-membered cyclic ring like certain kinds of prostaglandin.

Still another object of this invention is to provide a pharmaceutical use of the 5-membered cyclic compounds of the invention, especially their use as an antitumor agent.

Still another object of this invention is to provide novel 5-membered cyclic compounds which have better antitumor activity than hitherto known PG series.

Still another object of this invention is to provide novel 5-membered cyclic compounds as highly safe substances with antitumor activity which have no effect on normal cells and do not exhibit any significant toxicity.

Still another object of this invention is to provide novel 5-membered cyclic compounds which show nearly selective antitumor activity as a biological activity and do not substantially show hypotensive activity or platelet aggregation inhibiting activity exhibited by known $PGA_2$, and which are therefore very suitable for use as an antitumor agent.

Still another object of this invention is to provide a very simple process for producing the 5-membered cyclic compounds of the invention.

Further objects and advantages of this invention will become apparent from the following description.

As the novel cyclic 5-membered compounds of the invention, the present invention provides a 4,5-disubstituted-2-cyclopentenone selected from the group consisting of 5-alkylidene-4-substituted-2-cyclopentenones represented by the following formula (I)

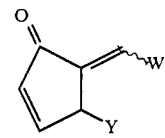

wherein W represents an aliphatic hydrocarbon group having 1 to 12 carbon atoms which may have a substituent, and Y represents an aliphatic hydrocarbon group having 1 to 12 carbon atoms which may have a substituent, and 5-(1-hydroxy aliphatic hydrocarbon)-4-substituted-2-cyclopentenones represented by the following formula (II)

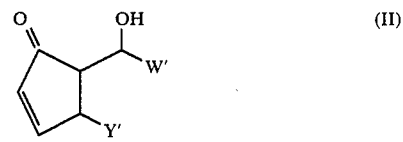

wherein W' and Y' are the same as W and Y above respectively. According to this invention, the 5-alkylidene-4-substituted-2-cyclopentenones of formula (I) can be produced by subjecting 5-alkylidene-3-hydroxy-4-substituted -cyclopentanones represented by the following formula (III)

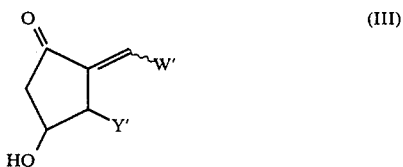

wherein W' and Y' are the same as W and Y above respectively, to dehydration reaction, and as required, subjecting the resulting product to a deprotecting, hydrolyzing or salt-forming reaction.

Some of the compounds of formula (III) are disclosed in European Laid-Open Patent Publication No. 0079733 and U.S. patent application Ser. No. 438,379, and are known. The compounds of formula (III) can be produced by converting a 3-hydroxy-5-(1-hydroxy-aliphatic hydrocarbon)-4-substituted-cyclopentanone represented by the following formula (IV)

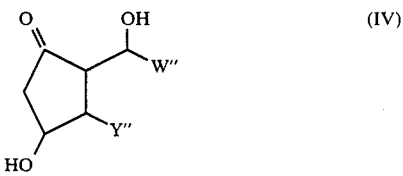

wherein W" and Y" are the same as W and Y above, respectively, to a corresponding 3-(t-butyldimethylsilyloxy)-5(1-methanesulfonyloxy-aliphatic hydrocarbon)-4-substituted-cyclopentanone, thereafter removing the methanesulfonyloxy group as methanesulfonic acid from the resulting cyclopentanone and further removing the t-butyldimethylsilyl group from it. Some of the compounds of formula (IV) are disclosed in European Laid-Open Patent Publications Nos. 0019475 and 0079733, U.S. Pat. No. 4,315,032 and U.S. Pat. Application Ser. No. 438379. The above process for producing the compound of formula (III) from the compound of formula (IV) is substantially the same as the methods described in European Laid-Open Patent Publication No. 0079733 and U.S. patent application Ser. No. 438,378. Accordingly, the disclosures of the above-cited European Laid-Open Patent Publications and U.S. Patent and U.S. patent application are incorporated herein as reference.

According to the present invention, the 5(1-hydroxyaliphatic hydrocarbon)-4-substituted-2cyclopentenones of formula (II) can be produced by subjecting a 5-(1-hydroxy-aliphatic hydrocarbon)3-hydroxy-4-substituted-cyclopentanone represented by the following formula (IV)

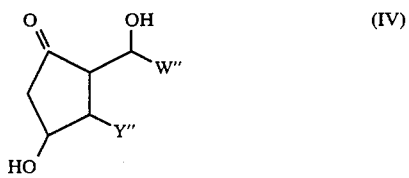

wherein W″ and Y″ are the same as W and Y above respectively, to dehydration reaction, and as required, subjecting the resulting product to a deprotecting, hydrolyzing or salt-forming reaction.

Now, the first process of this invention starting from the 5-alkylidene-3-hydroxy-4-substituted-cyclopentanone of formula (III) and the second process of the invention starting from the 5-(alpha-hydroxyaliphatic hydrocarbon)-3-hydroxy-4-substituted cyclopentanone of formula (IV) will be described in detail.

In the first process, W′ in formula (III) defining the starting material is an aliphatic hydrocarbon group having 1 to 12 carbon atoms, and Y′ is likewise an aliphatic hydrocarbon group having 1 to 12 carbon atoms. These aliphatic hydrocarbon groups may be substituted.

The aliphatic hydrocarbon groups for W′ and Y′ may be linear, branched or cyclic or may contain a carbon-carbon double or triple bond.

Preferably, the aliphatic hydrocarbon groups include, for example, linear or branched $C_{1-12}$ alkyl, alkenyl or alkynyl groups, and cycloalkyl groups having 3 to 8 carbon atoms.

Specific examples of alkyl groups having 1 to 12 carbon atoms are methyl, ethyl, n-propyl, isopropyl, n-butyl, sec-butyl, tert-butyl, n-pentyl, n-hexyl, n-heptyl, n-octyl, n-nonyl, n-decyl, n-undecyl and n-dodecyl.

Specific examples of the alkenyl groups having 1 to 12 carbon atoms are ethenyl, 1-propen-1-yl, 2-propen-1-yl, 1-buten-1-yl, 1,3-butadien-1-yl, 2-buten-1-yl, 1-penten-1-yl, 2-penten-1-yl, 1-hexen-1-yl, 2-hexen-1-yl, 1,5-hexadien-1-yl, 3-hexen-1-yl, 1-hepten-1-yl, 1-octen-1-yl, 1,7-octadien-1-yl, 1-nonen-1-yl, 1-decen-1-yl, 1-undecen-1-yl and 1- dodecen-1-yl.

Specific examples of the alkynyl groups having 1 to 12 carbon atoms are ethynyl, 1-propyn-1-yl, 2-propyn-1-yl, 1-butyn-1-yl, 3-buten-1-yne-1-yl, 2-butyn-1-yl, 1-pentyn-1-yl, 2-pentyn-1-yl, 1-hexyn-1-yl, 2-hexyn-1-yl, 5-hexen-1-yne-1-yl, 3-hexyn-1-yl, 1-heptyn-1-yl, 1-octyn-1-yl, 7-octen-1-yne-1-yl, 1-nonyn-1-yl, 1-decyn-1-yl, 1-undecyn-1-yl and 1-dodecyn-1-yl.

Examples of the cycloalkyl groups having 3 to 8 carbon atoms are cyclopropyl, cyclopentyl, cyclohexyl, cyclooctyl and cyclohexenyl.

These aliphatic hydrocarbon groups may have substituents.

Examples of the substituents include groups of the formula-13 $COOR^4$ (wherein $R^4$ represents a hydrogen atom, an alkyl group having 1 to 10 carbon atoms or one equivalent of a cation); groups of the formula $-OR^5$ (wherein $R^5$ represents a hydrogen atom, a $C_{1-6}$ alkyl which may be substituted by a halogen atom, a $C_{1-7}$ carboacyl group, or a phenyl group which may be substituted by a halogen atom, an alkyl group having 1 to 4 carbon atoms or an alkoxy group having 1 to 4 carbon atoms); a phenyl group which may be substituted by a halogen atom, an alkyl group having 1 to 4 carbon atoms, or an alkoxy group having 1 to 4 carbon atoms; and cycloalkyl groups having 3 to 8 carbon atoms which may be substituted by a halogen atom, an alkyl group having 1 to 4 carbon atoms or an alkoxy group having 1 to 4 carbon atoms.

Specific examples of the groups of the formula $-COOR^4$ are those in which $R^4$ is the same alkyl group as above having 1 to 10 carbon atoms, or one equivalent of a cation, for example an ammonium cation such as $NH_4^+$, tetramethyl ammonium, monomethyl ammonium, dimethyl ammonium, trimethyl ammonium, benzyl ammonium, phenethyl ammonium, morpholinium cation, monoethanol ammonium or piperidinium cation, an alkali metal cation such as $Na^{30}$ or $K^{30}$, or a divalent or trivalent metal cation such as $\frac{1}{2}Ca^{2+}$, $\frac{1}{2}Mg^{2+}\frac{1}{2}Zn^{2+}$ or $\frac{1}{3}Al^{3+}$.

Specific examples of the groups of the formula $-OR^5$ include a hydroxyl group; alkoxy groups having 1 to 6 carbon atoms such as methoxy, ethoxy, n-propoxy, isopropoxy, n-butoxy, n-pentoxy and n-hexoxy; carboacyloxy groups having 1 to 7 carbon atoms such as acetoxy, propionyloxy, n-butyryloxy, isobutyryloxy, n-valeryloxy, isovaleryloxy, caproyloxy, enanthyloxy and benzoyloxy; and a phenoxy group. The $C_{1-6}$ alkoxy groups for $-OR^5$ may be substituted by halogen atoms, thus providing chloromethoxy, dichloromethoxy, trifluoromethoxy, etc. The phenyl moiety of the phenoxy group for $-OR^5$ may be substituted by a halogen atom such as chloro, bromo or fluoro, an alkyl group having 1 to 4 carbon atoms such as methyl, ethyl, propyl or butyl, or an alkoxy group having 1 to 4 carbon atoms such as methoxy, ethoxy, propoxy or butoxy.

A phenyl group or a cycloalkyl group having 3 to 8 carbon atoms may also be substituents for the aforesaid aliphatic hydrocarbon groups. The phenyl group and the $C_{3-8}$ cycloalkyl group may be substituted by the same substituents as described above, i.e. a halogen atom, an alkyl group having 1 to 4 carbon atoms or an alkoxy group having 1 to 4 carbon atoms. According to this invention, the aforesaid first process which comprises subjecting the 5-alkylidene-3-hydroxy-4-substituted cyclopentenone of formula (III) to dehydration reaction and as required subjecting the resulting product to a deprotecting, hydrolyzing or salt-forming reaction is preferably performed by producing a 5-alkylidene-4-substituted-2-cyclopentenone represented by the following formula (I)-1

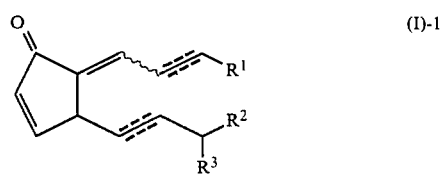

wherein R¹ represents a hydrogen atom or an aliphatic hydrocarbon group having 1 to 10 carbon atoms which may have a substituent, R² represents a hydrogen atom, or an aliphatic hydrocarbon group having 1 to 9 carbon atoms which may have a substituent, R³ represents a hydrogen atom, a hydroxyl group, or a protected hydroxyl group, and the symbol ≡≡≡≡ represents a single, double or triple bond, from a 5-alkylidene-3-hydroxy-4-substituted cyclopentenone represented by the following formula (III)-1

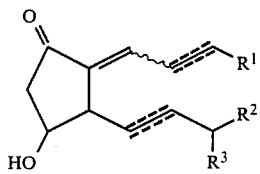

wherein R¹, R², R³, and the symbol ≡≡≡≡ are the same as given for formula (I)-1. The dehydration reaction of the 5-alkylidene-3-hydroxy-4-substituted cyclopentenone of formula (III) or (III)-1 is preferably carried out in the presence of a dehydrating agent. Examples of the dehydrating agent include inorganic acids such as hydrochloric acid, hydrobromic acid, hydrofluoric acid and phosphoric acid, organic carboxylic acids such as propionic acid, oxalic acid, citric acid and maleic acid, and organic sulfonic acids such as methanesulfonic acid, ethanesulfonic acid, benzenesulfonic acid and p toluenesulfonic acid. Of these, the inorganic acids and organic carboxylic acids are preferred. The amount of the dehydrating agent used is preferably 0.5 to 100 moles, especially preferably 1 to 50 moles per mole of the 5-alkylidene-3-hydroxy-4-substituted cyclopentenone. As a reaction solvent, there may be used an ether such as tetrahydrofuran, dioxane, dimethoxyethane or diethyl ether, an alcohol such as methanol or ethanol, dimethyl sulfoxide, dimethylformamide, hexamethylphosphoric triamide, acetonitrile, and water, either singly or in combination with each other.

The reaction temperature is preferably 0° to 80° C., especially preferably 10° to 50 ° C.

The reaction time varies depending upon the starting compound, the dehydrating agent and the reaction solvent used in the reaction. Usually, it is 10 minutes to 10 days, preferably 20 minutes to 5 days.

The 5-alkylidene-3-hydroxy-4-substituted cyclopentenone of formula (III) [including formula (III)-1]can be produced, for example, in accordance with the following reaction formula.

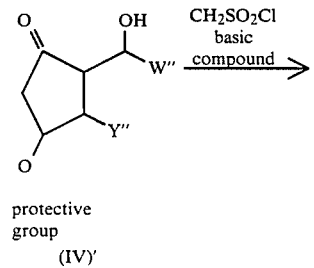

protective
group
(IV)'

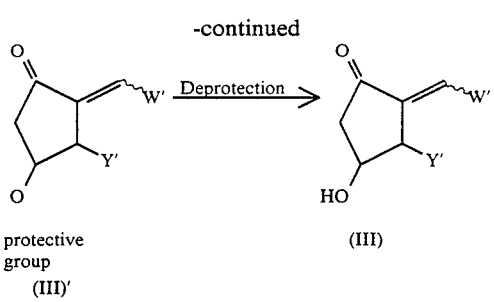

protective (III)
group
(III)'

Specifically, it can be produced by reacting the corresponding 3-hydroxy-5-(1-hydroxy-aliphatic hydrocarbon)-4-substituted cyclopentanone derivative of formula (IV)' with methanesulfonyl chloride in the presence of a basic compound and then eliminating the protective group.

As can be understood from the above reaction formula, it is possible to subject the 5-alkylidene-3-hydroxy-4-substituted cyclopentanone of formula (III)' in which the 3-position hydroxyl group is protected by a t-butyldimethylsilyl group to a deprotection reaction using a deprotecting aid such as acetic acid thereby removing the protective group at the 3-position and forming the 5-alkylidene-3-hydroxy-4 -substituted cyclopentanone in situ, and subsequently to subject this reaction mixture to the dehydration reaction in accordance with this invention.

According to the dehydration reaction of this invention, a corresponding compound (final desired compound) having a double bond formed between the 2-and 3-positions in formula (II) as a result of removal of the 3-position hydroxyl group is formed. When the resulting final compound has in the group W' and/or Y' a group removable by hydrolysis or deprotection or a group capable of forming a salt by salt-forming forming reaction and it is desired to obtain a final product by hydrolysis, deprotection or salt-forming reaction, the above dehydration reaction in the process of this invention can be followed by such a reaction.

Groups capable of being removed by hydrolysis are, for example, carboacyl groups or ester groups. The carboacyl groups can be hydrolyzed, for example, in an aqueous solution of sodium hydroxide, potassium hydroxide or calcium hydroxide, a water-alcohol mixture, a methanol or ethanol solution containing sodium methoxide, potassium methoxide or sodium ethoxide. The ester groups can be hydrolyzed, for example, in water or a solvent containing water at a temperature of −10° C. to +60° C. for a period of about 10 minutes to about 24 hours using an enzyme such as lipase.

Groups capable of being removed by deprotection are, for example, groups forming an acetal linkage with the oxygen atom of the hydroxyl group, or tri($C_{1-7}$ hydrocarbon)silyl groups. The removal of the protective group can be performed suitably, for example by using acetic acid, a pyridinium salt of p-toluenesulfonic acid, a cation exchange resin, etc. as a catalyst and water, tetrahydrofuran, diethyl ether, dioxane, acetone, acetonitrile, etc. as a reaction solvent when the protective group is a group forming an acetal linkage together with the oxygen atom of the hydroxyl group. The reaction is carried out usually at a temperature of −78° C. to +30° C. for about 10 minutes to about 3 days. When the protective group is a tri($C_{1-7}$ hydrocarbon)silyl group, the deprotecting reaction may be carried out in the presence of acetic acid, tetrabutyl ammonium fluoride, cesium fluoride, etc. in the same reaction solvent as cited above at the same temperature and for the same period of time as mentioned above.

When the final compound has a carboxyl group in the molecule, it can then optionally be subjected to a salt-forming reaction to obtain the final compound as a carboxylate salt. The salt-forming reaction is known per se, and is carried out by neutralizing the carboxylic acid with a nearly equivalent of a basic compound such as sodium hydroxide, potassium hydroxide or sodium carbonate, or ammonia, trimethylamine, monoethanolamine or morpholine in a customary manner. The final desired compound can be isolated and purified, for example, by silica gel column chromatography, silica gel thin-layer chromatography, high-performance liquid chromatography, Florisil column chromatography, etc.

The 5-alkylidene-4-substituted-2-cyclopentenones of formula (I) in accordance with this invention can also be produced by treating the 5-(1-hydroxy-aliphatic hydrocarbon)-4-substituted-2-cyclopentenones of formula (II) with methanesulfonyl chloride in the presence of basic compounds. The basic compounds may be amines such as dimethylaminopyridine, triethylamine, isopropylcyclohexylamine, isopropyldimethylamine and diisopropylamine. A reaction solvent may be used, and examples include halogenated hydrocarbons such as dichloromethane, chloroform, carbon tetrachloride, ethers such as diethyl ether and tetrahydrofuran, and aromatic hydrocarbons such as benzene and toluene. Methanesulfonyl chloride is used generally in an amount of 1 to 10 moles per mole of the 5-(1-hydroxy-aliphatic hydrocarbon)-4-substituted-2-cyclopentenone of formula (II), and the reaction temperature may be from 0° to 50° C., preferably 15° to 25° C. The method disclosed in European Laid-Open Patent Publication No. 0079733 may be referred to in performing the above process.

In the second process of this invention, W'' in formula (IV) defining the starting material is an aliphatic hydrocarbon group having 1 to 12, and Y'' is likewise an aliphatic hydrocarbon group having 1 to carbon atoms. These aliphatic hydrocarbon groups may be substituted. Specific examples of W'' and Y'' may be the same as those given hereinabove for W' and Y'.

According to this invention, the second process is preferably carried out by producing a 4-substituted-5-(1-hydroxy-aliphatic hydrocarbon)-2-cyclopentenone represented by the following formula (II)-1

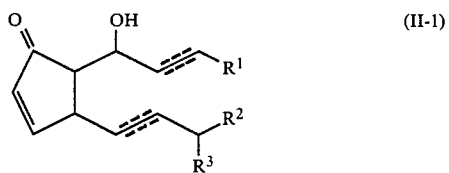
(II-1)

wherein $R^1$, $R^2$, $R^3$ and the symbol ≅≅≅≅ are the same as defined for formula (III)-1 above, from a 5-(1-hydroxy-aliphatic hydrocarbon)-3-hydroxy-4-substituted cyclopentanone represented by the following formula (IV)-1

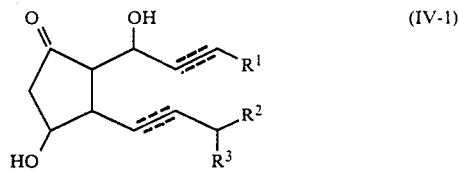
(IV-1)

wherein $R^1$, $R^2$, $R^3$, and the symbol ≅≅≅≅ are the same for formula (II)-1. The dehydration reaction of the compound of formula (IV) or (IV)-1 can be carried out under quite same reaction conditions as in the aforesaid first process. In this reaction, the reaction temperature is preferably 0° to 130° C., especially preferably 30° to 110° C.

Deprotection, hydrolysis and salt-forming reaction can all be carried out in quite the same ways as described in regard to the first process Thus, according to this invention, there are provided 5-alkylidene-4-substituted-2-cyclopentenones represented by the following formula (I)

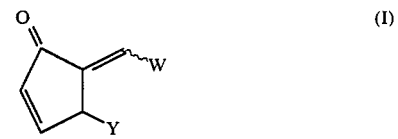
(I)

wherein W and Y are as defined above, and 5-(1-hydroxy-aliphatic hydrocarbon)-4-substituted- 2 -cyclopentenones represented by the following formula (II)

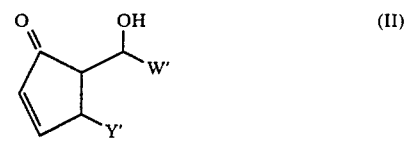
(II)

wherein W' and Y' are as defined above, as novel 5-membered cyclic compounds.

Among the compounds of formula (I), those of the following compounds (I)-1

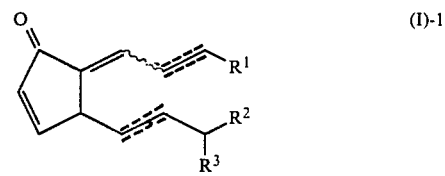
(I)-1 wherein $R^1$ represents a hydrogen atom, or an aliphatic hydrocarbon group having 1 to 10 carbon atoms which may be substituted, $R^2$ represents a hydrogen atom, or an aliphatic hydrocarbon group having 1 to 9 carbon atoms which may be substituted, $R^3$ represents a hydrogen atom, a hydroxyl group or a protected hydroxyl group, and the symbol ≅≅≅≅ represents a single, double or triple bond, are preferred, and those of the following formula (I)-2

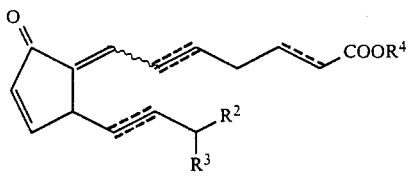

wherein $R^2$, $R^3$, $R^4$ and the symbol ≡≡≡≡ are as defined above, and the symbol ≡≡≡≡ represents a single or double bond, (A-type prostaglandins) are especially preferred.

$R^1$ in formulae (I)-1 and (II)-1 represents a hydrogen atom or an aliphatic hydrocarbon group having 1 to 10 carbon atoms. The aliphatic hydrocarbon group may be substituted.

The aliphatic hydrocarbon group having 1 to 10 carbon atoms may be linear, branched or cyclic, and may have a carbon-carbon double bond.

Examples of preferred aliphatic hydrocarbon groups having 1 to 10 carbon atoms include linear or branched alkyl or alkenyl groups and cycloalkyl groups having 3 to 8 carbon atoms.

Specific examples of the alkyl groups having 1 to 10 carbon atoms include methyl, ethyl, n-propyl, iso-propyl, n-butyl, sec-butyl, tert-butyl, n-pentyl, n-hexyl, n-heptyl, n-octyl, n-nonyl and n-decyl.

Specific examples of the alkenyl groups having 1 to 10 carbon atoms include ethenyl, 1-propen-1-yl, 2-propen-1-yl, 3-buten-1-yl, 1-buten-1-yl, 4-penten-1-yl, 5-hexen-1-yl, 6-penten-1-yl, 7-octen-1-yl, 8-nonen-1-yl and 9-decen-1-yl. Of these, 1-propen-1-yl, 2-propen-1-yl, 3-buten-1-yl, 4-penten-1-yl and 5-hexen-1-yl are preferred.

Examples of the cycloalkyl groups having 3 to 8 carbon atoms are the same as those given for W' and Y' in formula (III).

$R^2$ in formulae (I)-1, (I)-2, (II)-1 and (II)-2 represents a hydrogen atom or an aliphatic hydrocarbon group having 1 to 9 carbon atoms. The aliphatic hydrocarbon group may be substituted.

Examples of the aliphatic hydrocarbon groups having 1 to 9 carbon atoms include linear or branched alkyl groups such as methyl, ethyl, n-propyl, isopropyl, n-butyl, sec-butyl, t-butyl, n-pentyl, n-hexyl, 2-methyl-1-hexyl, 2-methyl-2-hexyl, n-heptyl and n-octyl, and the same $C_{3-8}$ cycloalkyl groups as exemplified above. $R^3$ in formulae (I)-1, (I)-2, (II)-1 and (II)-2 represents a hydrogen atom, a hydroxyl group or a protected hydroxyl group. Examples of the protective group for the hydroxyl group are tri($C_{1-7}$ hydrocarbon)silyl groups and groups forming an acetal linkage with the oxygen atom of the hydroxyl group.

Specific examples of preferred tri($C_{1-7}$ hydrocarbon)silyl groups include tri($C_{1-4}$ alkyl)silyl groups such as trimethylsilyl, triethylsilyl or t-butyldimethylsilyl, diphenyl($C_{1-4}$ alkyl)silkyl groups such as t-butyldiphenylsilyl, and a tribenzylsilyl group.

Examples of the groups forming an acetal linkage together with the oxygen atom of the hydroxyl group include methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxo-bicyclo[3.1.0]-hex-4-yl groups. Of these, 2-tetrahydropyranyl, 2-tetrahydrofuranyl, 1-ethoxyethyl, 2-methoxy-2propyl, (2-methoxyethoxy)methyl and 6,6-dimethyl-3-oxa-2-oxo-bicyclo[3.1.0]hex-4-yl groups are particularly preferred.

The following examples are given for the novel cyclic 5-membered compounds of the above formulae (I) [including formulae (I)-1 and (I)-2] and (II) [including formulae (II)-1 and (II)-2].

(i) Compounds of formula (I)

(100) 4-Butyl-5-(6-carboxyhexylidene)-2-cyclopentenone, (102) 4-octyl-5-(6-carboxyhexylidene)-2-cyclopentenone, (104) 4-(1-octenyl)-5-(6-carboxyhexylidene)-2-cyclopentenone, (106) 4-(3-hydroxy-1-octenyl)-5-(6-carboxy-hexylidene)-2-cyclopentenone, (108) 4-(3-hydroxy-3-cyclohexyl-1-propenyl)-5-(6-carboxyhexylidene)-2-cyclopentenone, (110) 4-(3-hydroxy-3-cylopentyl-1-propenyl)-5-(6-carboxyhexylidene)-2-cyclopentenone, (112) 4-(2-propenyl)-5-(6-carboxyhexylidene)-2-cyclopentenone, (114) 4-(3-hydroxy-5-methyl-nonenyl)-5-(6-carboxyhexylidene)-2-cyclopentenone, (116) 4-(3 hydroxy-3-phenyl-1-propenyl)-5(6-carboxyhexylidene)-2-cyclopentenone, (118) 4-(1-hydroxy-3-phenyl-1-propenyl)-5(6-carboxyhexylidene)-2-cyclopentenone, (120) 4-(3-hydroxy-3-methyl-1-propenyl)-5(6-carboxyhexylidene)-2cyclopentenone, (122) 4-(3-hydroxy-5,5-dimethyl-1-octenyl)-5-(6-carboxyhexylidene)-2-cyclopentenone, (124) 4-(3-hydroxy-4-p-henoxy-1-butenyl) -5-(6-carboxyhexylidene)-2-cyclopentenone, (126) 4-butyl-5-(6-carboxy-2-hexenylidene)-2-cyclopentenone, (128) 4-butyl-5-(6-carboxy-2-hexynylidene)-2-cyclopentenone, (130) 4-butyl-5-(6-carboxy-5-hexenylidene)-2-cyclopentenone, (132) 4-octenyl-5-(6-carboxy-2-hexenylidene)-2-cyclopentenone, (134) 4-octenyl-5-(6-carboxy-2-hexenylidene)-cyclopentenone, (136) 4-(3-hydroxy-1-octenyl)-5-(6-carboxy-2-hexynylidene)-2-cyclopentenone, (138) 4-(3-hydroxy-3-cyclopentyl-1-propenyl)-5-(6-carboxy-2-hexenylidene)-2-cyclopentenone, (140) 4-(3-hydroxy-3-cyclohexyl-1-propenyl) -5-(6-carboxy-2-hexynylidene)-2-cyclopentenone, (142) 4-butyl-5-(2-methylpropylidene)-2-cyclopentenone, (144) 4-butyl-5-(2,2-dimethylpropylidene)-2-cyclopentenone, (146) 4-(3-hydroxy-1-octenyl)-5-butylidene-2-cyclopentenone, (148) 4-butyl-5-(3-phenyl-2-propenylidene)-2-cyclopentenone, (150) 4-octyl-5-(2-methylpropylidene)-2-cyclopentenone, (152) 4-(1-octenyl)-5-(6-carboxy-2-hexenyl-idene)-2-cyclopentenone, (154) 4-butyl-5-heptylidene-2-cyclopentenone, (156) 4-octyl-5-heptylidene-2-cyclopentenone, (158) 4-(3-hydroxy-1-octenyl)-5-heptylidene-2-cyclopentenone, (160) 4-butyl-5-(7-hydroxyheptylidene)-2-cyclopentenone, (162) 4-octyl-5-(7-hydroxyheptylidene)-2-cyclopentenone,
(164) 4-(3-hydroxy-1-octenyl)-5-(7-hydroxyheptylidene)-2-cyclopentenone,
(166) 4-(1-octenyl)-5-(7-hydroxyheptylidene)-2-cyclopentenone,
(168) 4-(3-hydroxy-4-m-fluorophenoxy)-5-(6-carboxyhexylidene)2-cyclopentenone,
(170) 4-(3-hydroxy-4-m-trifluoromethylphenyl)-5-(6-carboxyhexylidene)-2-cyclopentenone,
(172) 4-(1-octyne)-5-(6-carboxyhexylidene)-2-cyclopentenone,
(174) methyl ester of (100),
(176) methyl ester of (102),
(178) methyl ester of (104),
(180) methyl ester of (106),
(182) ethyl ester of (108),
(184) ethyl ester of (110),
(186) ethyl ester of (112),
(188) propyl ester of (114).
(190) propyl ester of (120),
(192) sodium salt of (124),
(194) sodium salt of (126),
(196) sodium salt of (128),
(198) aluminum salt of (130),
(200) aluminum salt of (136),
(202) aluminum salt of (138),
(204) aluminum salt of (140), (ii) Compound of formula II (300) 4-butyl-5-(1-hydroxybutyl)-2-cyclopentenone,
(302) 4-butyl-5-(1-hydroxy-1-methylpropyl)-2-cyclopentenone,
(304) 4-butyl-5-(1-hydroxy-2,2-dimethylpropyl)-2-cyclopentenone,
(306) 4-butyl-5-(1-hydroxy-3-phenyl-2-propen-1)-2-cyclopentenone,
(308) 4-butyl-5-(1-hydroxybutyl)-2-cyclopentenone,
(310) 4-octyl-5-(1-hydroxybutyl)-2-cyclopentenone,
(312) 4-(2-propenyl)-5-(1-hydroxybutyl)-2-cyclopentenone,
(314) 4-(1-octenyl)-5-(1-hydroxybutyl)-2-cyclopentenone,
(316) 4-(3-hydroxy-1-octenyl)-5-(1-hydroxy-butyl)-2-cyclopentenone,
(318) 4-butyl-5-(1-hydroxy-6-carboxyhexyl)-2-cyclopentenone,
(320) 4-octyl-5-(1-hydroxy-6-carboxyhexyl)-2-cyclopentenone,
(322) 4-(1-octenyl)-5-(1-hydroxy-6-carboxy-hexyl)-1-cyclopentenone,
(324) 4-decyl-5-(1-hydroxy-6-carboxyhexyl)-2-cyclopentenone,
(326) 4-(5-methyl-1-nonenyl)-5-(1-hydroxy-6-carboxyhexyl)-2-cyclopentenone,
(328) 4-(3-hydroxy-5-methyl-1-nonenyl)-5-(1-hydroxy-6-carboxyhexyl)-2-cyclopentenone,
(330) 4-(3-cyclohexyl-1-propenyl)-5-(1-hydroxy-carboxyhexyl)-2-cyclopentenone,
(332) 4-(1-octenyl)-5-(1-hydroxy-8-carboxyoctyl)-2-cyclopentenone,
(334) 4-(1-octenyl)-5-(1-hydroxy-5-carboxypentyl)-2-cyclopentenone,
(336) 4-(3-hydroxy-1-octenyl)-5-(1-hydroxy-6-caboxyhexyl)-2-cyclopentenone,
(338) 4-(3-hydroxy-1-octenyl)-5-(1-hydroxy-6carboxy-5-hexene-1-yl)-2-cyclopentenone,
(340) 4-(3-hydroxy-1-octenyl)-5-(1-hydroxy-6-carboxy-3-hexene-1 yl)-2-cyclopentenone,
(342) 4-(3-hydroxy-1-octenyl)-5-(1-hydroxy-6 carboxy-2-hexene-1-yl)-2-cyclopentenone,
(344) 4-(3-hydroxy-5-methyl-1-nonenyl)-5-(1-hydroxy-6-carboxy-5-hexene-1-yl)-2-cyclopentenone,
(346) 4-(3-hydroxy-4-methyl-1-nonenyl)-5-(1-hydroxy-6-carboxy-2-hexyne-1-yl)-2-cyclopentenone,
(348) 4-(3-hydroxy-3-cyclohexyl-1-propenyl)-5-(1-hydroxy-6-carboxy-2-hexyne-1-yl)-2-cyclopentenone,
(350) 4-(3-hydroxy-3-cyclohexyl-1-propenyl)-5-(1-hydroxy-8-carboxy-2-octyne-1-yl)-2-cyclopentenone,
(352) 4-(3-hydroxy-4-cyclohexyl-1-butenyl)-5-(1-hydroxy-6-carboxy-4-hexene-1-yl)-2-cyclopentenone,
(354) 4-(3-hydroxy-3-cyclopentyl-1-propenyl)-1-(1-hydroxy-6-carboxyhexyl)-2-cyclopentenone,
(356) 4-(3-hydroxy-3-phenoxy-1-propenyl)-5-(1-hydroxy-6-carboxyhexyl)-2-cyclopentenone,
(358) 4-(3-hydroxy-4-phenoxy-1-butene)-5-(1-hydroxy-6-carboxyhexyl)-2-cyclopentenone,
(360) 4-(3-hydroxy-4,4-dimethyl-1-octenyl)-5-(1-hydroxy-6-carboxyhexyl)-2-cyclopentenone,
(362) 4-(3-hydroxy-5,5-dimethyl-1-octenyl)-5-(1-hydroxy-6-carboxyhexyl)-2-cyclopentenone,
(364) methyl ester of (300),
(366) methyl ester of (302),
(368) methyl ester of (304),
(370) methyl ester of (306),
(372) ethyl ester of (308),
(374) ethyl ester of (310),
(376) ethyl ester of (314).
(378) propyl ester of (320),
(380) propyl ester of (324),
(382) sodium salt of (330),
(384) sodium salt of (334),
(386) sodium salt of (350),
(388) aluminum salt of (352).
(390) aluminum salt of (356),
(392) aluminum salt of (358).

Investigations of the present inventors have shown that the novel cyclic 5-membered compounds of this invention, i.e. the 5-alkylidene-4-substituted 2-cyclopentenones of formula (I) and the 5-(alpha-hydroxy-aliphatic hydrocarbon)-4-substituted-2-cyclopentenones of formula (II), and the 5-alkylidene-3-hydroxy-4-substituted cyclopentanones of formula (III) used as starting materials for the production of the compounds of formula (I) in the first process of this invention have excellent pharmacological activities.

Accordingly, the present invention also provides a pharmaceutical composition comprising as an active ingredient a 5-membered cyclic compound selected from the group consisting of the 5-alkylidene-4-substituted-2-cyclopentenones of formula (I), the 5-(1-hydroxy-hydrocarbon)-4-substituted-2-cyclopentenones of formula (II), and the 5-alkylidene-3-hydroxy-4-substituted cyclopentanones of formula (III), and a pharmaceutically acceptable carrier.

The 5-membered cyclic compounds of formulae (I), (II) and (III) in accordance with this invention exhibit strong anticancer activity in low concentrations against L1210 leukemia cells and are very useful as antitumor agents. They are also useful as compounds having antiviral activity.

According to this invention, the 5-membered cyclic compounds can be administered orally, or parenterally through intrarectal, subcutaneous, intramuscular and intravenous routes, for example. For oral administration, the compounds of this invention may be formulated into solid or liquid preparations. Examples of the solid preparations are tablets, pills, powders and granules. In these solid preparations, at least one of the 5-membered cyclic compounds is mixed with sodium bicarbonate, calcium carbonate, potato starch, sucrose, mannitol, carboxymethyl cellulose, etc. These preaprations can be formed in accordance with customary operations. The solid preparations may also include a lubricant, a sweetener, a stabilizer, an antiseptic, etc. such as calcium stearate, magnesium stearate or glycerol.

Examples of the liquid preparations for oral administration are emulsions, solutions, suspensions, syrups, and elixirs. The liquid preparations may further include a wetting agent, a suspending aid, a sweetener, a flavor, an aroma, a stabilizer, etc. The liquid preparations may be filled in capsules made of an absorbable material such as gelatin.

For intrarectal administration, ordinary suppositories such as soft gelatin capsules are used.

Examples of preparations for parenteral administration through other routes are preparations for subcutaneous, intramuscular or intravenous injection in the form of aseptic aqueous or non-aqueous solutions, suspensions and emulsions. The nonaqueous solutions and suspensions may include propylene glycol, polyethylene glycol, olive oil or injectable organic esters such as ethyl oleate. Such preparations may also contain an antiseptic, an emulsifier, a dispersant, a stabilizer, etc. These injectable preparations can be made aseptic by filtration through a bacteria-holding filter, blending of a germicide, or irradiation.

The dose of the 5-membered cyclic compound of this invention differs depending upon the condition, age, sex and body weight of a subject to which it is to be administered, the route of administration, etc. Usually, it can be administered in a dose of about $1\mu g$ to 100 mg/kg-body weight/day. The dose may be a single dose, or may be divided into several portions, for example 2 to 6 portions.

The pharmaceutical composition of this invention is preferably used as a medicament in unit dosage form.

The following Examples illustrate the present invention in greater detail.

EXAMPLE 1

Synthesis of (7E)-7,8-dehydro $PGE_1$ (1) 450 mg (0.75 mmole) of 7-hydroxy $PGE_1$ 11,15-bis (t-butyldimethylsilyl)ether was dissolved in 7 ml of anhydrous dichloromethane, and 367 mg (30 mmoles) of dimethylaminopyridine was added. Methanesulfonyl chloride (116 microliters; 1.5 mmoles) was added, and the mixture was stirred at room temperature for 16 hours. A saturated aqueous solution of sodium chloride was added, and the mixture was adjusted to pH 2 with oxalic acid and extracted with dichloromethane. The extract was dried over anhydrous magnesium sulfate, filtered, concentrated and subjected to silica gel column chromatography (silica gel 20 g; eluent, hexane:acetone=20:1→5:1) to give 72 mg (yield 16%) of (7E)-7,8-dehydro $PGE_1$ 11,15-bis-(t-butylmethylsilyl)ether and 17 mg (yield 4%) of (7Z)-7,8-dehydro $PGE_1$ 11,15-bis(t-butyldimethyl-silyl)ether.

Spectral data of (7E)-7,8-dehydro $PGE_1$ 11,15-butyl-dimethylsilyl)ether:
TLC: Rf=0.43 (hexane:acetone=2:1)
IR (liquid film):
3600–2400, 1713, 1650, 1461, 1255, 1073, 833 772, 929 $cm^{-1}$.
NMR $(CDCl_3)\delta$: 0–0.2 (m, 12H), 0.84 (s, 9H), 0.87 (s, 9H), 0.7–1.1 (m, 3H), 1.0–3.0 (m, 20H), 3.2–3.7 (m, 1H), 3.8–4.3 (m, 2H), 5.3–5.7 (m, 2H), 6.66 (dt, 1H, J=7.5, 2.0 Hz), 9.0–9.8 (m, 1H).

Spectral data of (7E)-7,8-dehydro $PGE_1$ 11,15-bis(t-butyldimethylsilyl)ether:
TLC: Rf=0.52 (hexane:acetone=2:1)
IR (liquid film): 3600–2400, 1740, 1648, 1460, 1254, 1077, 836, 773, 757 $cm_{31}$.
NMR $(CDCl_{13})\delta$: 0–0.2 (m, 12H), 0.88 (s, 9H), 0.90 (S, (H), 0.7–1.1 (m, 3H), 1.0–3.0 (m, 20H), 3.3–3.5 (m, 1H), 3.8–4.3 (m, 2H), 4.8–6.0 (m, 1H), 5.4–5.8 (m, 2H)

(2) 22 mg (38 micromoles) of (7E)-7,8-dehydro $PGE_1$ 11,15-bis(t-butyldimethylsilyl)ether was added to 1.0 ml of a hydrogen fluoride-acetonitrile solution (prepared by adding 0.5 ml of 47% hydrofluoric acid to 10 ml of acetonitrile), and the mixture was stirred at room temperature for 20 minutes. A saturated aqueous solution of sodium bicarbonate was added, and the mixture was acidified with oxalic acid and extracted with ethyl acetate. The organic layer was washed with a saturated aqueous solution of sodium chloride, and dried over anhydrous magnesium sulfate. The dried product was filtered, concentrated and subjectd to silica gel thin-layer chromatography (developing solvent, hexane:acetone:acetic acid=1:1:0.01) to give 3.7 mg (yield 28%) of (7E)-7,8-dehydro $PGE_1$.

Spectral data of (7E)-7,8-dehydro PGE1:
TLC: Rf=0.47 (hexane:acetone=1:2)
IR $(CHCl_3$ solution): 3400, 1715, 1642, 973 $cm^{-1}$.
NMR $(CDCl_3)\delta$: 0.88 (brt, 3H), 1.0–1.9 (m, 14H), 1.9–2.9 (m, 5H), 2.9–3.9 (m, 5H), 3.9–4.5 (m, 2H), 5.3–5.9 (m, 2H), 6.7–7.0 (m, 1H).

EXAMPLE 2

Synthesis of (7E)-7,8-dehydro $PGA_1$ 160 mg of (7E)-7,8-dehydroprostaglandin $E_1$ was dissolved in 3 ml of tetrahydrofuran, and 2 ml of 0.5N hydrochloric acid was added. The mixture was stirred at room temperature for 4 days. A saturated aqueous solution of sodium chloride was added, and the mixture was extracted with ethyl acetate. The organic layers were combined, washed with a saturated aqueous solution of sodium chloride and dried over anhydrous magnesium sulfate. The dried product was filtered, concentrated and purified by silica gel thin-layer chromatography to give 95 mg (yield 63%) of (7E)-7,8-dehydroprostaglandin $A_1$.

TLC: Rf=0.58 (developing solvent, hexane:acetone=1:2)

IR ($CHCL_3$ solution): 3650–2400, 1698, 1646. 967 $cm^{-1}$.

NMR ($CDCl_3$)δ:
0.88 (t, 3H, J=6.0 Hz), 1.0–2.0 (m, 14H), 2.0–2.8 (m, 4H), 3.4–4.6 (m, 4H), 5.1–5.9 (m, 2H), 6.34 (dd, 1H, J=6.0, 2.4 Hz), 6.61 (dd, 1H, J=7.8, 1.5 Hz), 7.36 (dd, 1H, J=6.0, 2.7 Hz).

EXAMPLE 3

Synthesis of (7E)-7,8-dehydro $PGA_1$ 22 mg of (7E) 7,8-dehydroprostaglandin $E_1$, 11,15-bis(t-butylmethylsilyl)ether was dissolved in a solution containing 1 ml of acetonitrile and 50 microliters of 47% hydrofluoric acid, and the mixture was stirred at room temperature for 20 minutes. A saturated aqueous solution of sodium bicarbonate was added, and the mixture was adjusted to pH 1 with oxalic acid, and extracted with ethyl acetate. The organic layers were combined, washed with a saturated aqueous solution of sodium chloride, and dried over anhydrous magnesium sulfate. The dried product was filtered, concentrated and purified by silica gel thin-layer chromatography to give 4.7 mg (yield 37%) of (7E)-7,8-dehydroprostaglandin $A_1$.

EXAMPLE 4

Synthesis of (7E)-7,8-dehydro $PGA_1$ methyl ester and 12-epi-(7E)-7,8-dehydro $PGA_1$ methyl ester:

1.0 mg of a mixture of (7E)-7,8-dehydro $PGE_1$ methyl ester 11,15-bis(t-butyldimethylsilyl)ether and 15-epi-ent-(7E)-7,8-dehydro $PGE_l$ methyl 11,15bis-(t-butyldimethylsilyl)ether was suspended in a mixed solvent consisting of acetic acid, tetrahydrofuran and water in a ratio of 2:1:1, and the suspension was stirred at 50° for 14 hours and the at 60° C. for 3 hours. After concentration, water and sodium carbonate were added to the residue to perform neutralization. The mixture was extracted with ethyl acetate. The organic layer was washed with a saturated aqueous solution of sodium chloride, dried over anhydrous magnesium sulfate, filtered, concentrated, and subjected to silica gel column chromaotgraphy (silica gel 200 g; hexane:ethyl acetate=1:1) to give 184 mg (yield 1%) of 12-epi-(7E)-7,8-dehydro $PGA_1$ methyl ester and 184 mg (yield 31%) of (7E)-7,8-dehydro $PGA_1$ methyl ester.

Spectral data of 12-epi-(7E)-7,8-dehydro $PGA_1$ methyl ester:

TLC: Rf=0.57 (hexane:ethyl acetate=1:3)

IR (liquid film): 3560, 1738, 1700, 1648, 1577 $cm^{-1}$.

NMR ($CDCL_3$)δ: 0.90 (brt, 3H), 1.0–2.0 (m, 14H), 2.0–2.7 (m, 5H), 3.66 (s, 3H), 3.75–4.45 (m, 2H), 5.45 (dd, 1H, J=15.5, 6.5 Hz), 5.71 (dd, 1H, J=15.5, 6.0Hz)m, 6.30 (dd, 1H, J=6.0, 2.0Hz), 6.63 (brt, 1H, J=8.0 Hz), 7.41 (dd, 1H, J=6.0, 3.0 Hz).

Spectral data of (7E)-7,8-dehydro $PGA_1$ methyl ester:

TLC. Rf=0.51 (hexane:ethyl acetate=1:3)

IR (liquid film): 3450, 1739, 1701, 1648, 1578 $cm^{-1}$.

NMR ($CDCl_3$)δ: 0.90 (brt, 3H), 1.0–2.0 (m, 14H), 2.0–2.8 (m, 5H), 3.66 (s, 3H), 3.7–4.5 (m, 2H), 5.46 (dd, 1H, J=15.5, 6.5 Hz), 5.71 (dd, 1H, J=15.5, 6.0 Hz), 6.34 (dd, 1H, J=6.0, 2.0 Hz), 6.63 (brt, 1H, J=8.0 Hz), 7.41 (dd, 1H, J=6.0, 3.0 Hz).

EXAMPLE 5

Synthesis of 4-(1-octenyl)-5-(6-methoxy-carbonylhexylidene)-2-cycopentenone:

1) 3.1 g (6.4 millinmols) of 4-(1-octenyl)-5-(1-hydroxy-6-methoxycarbonylhexyl)-3-(t-butyldimethylsilyloxy)cyclopentanone was dissolved in 40 ml of dichloromethane, and 3.92 g (32.1 mmoles) of dimethylaminopyridine was added. With ice cooling and stirring, 1.0 ml (12.9 mmoles) of methanesulfonyl chloride was added. The mixture was stirred at 0° C. for 5 minutes, and then at room temperature for hours. Furthermore, 0.78 g (6.4 millimoles) of dimethylaminopyridine was added, and the mixture was stirred for 100 minutes. The mixture was poured into 200 ml of 0.5N hydrochloric acid and washed. The aqueous layer was extracted with dichloromethane. The organic layers were combined, washed first with a saturated aqueous solution of sodium bicarbonate and then with a saturated aqueous solution of sodium chloride, and dried over anhydrous sodium sulfate. The dried product was filtered, concentratd and subjected to silica gel column chromatography (silica gel 150 g; eluent, hexane:ethyl acetate=20:1 →7:1) to give 1.83 g (yield 61%) of 4-(1-octenyl)-5-(6-methoxycarbonylhexylidene)-3-(t-butyldimethylsilyloxy) cyclopentanone. The spectral data of this compound were as follows.

TLC: Rf=0.45 (hexane:ethyl acetate=5:1)

NMR ($CDCl_3$)δ: 0–0.2 (m, 6H), 0.83 (s, 9H), 0.7–1.1 (m, 3H), 1.0–2.8 (m, 22H), 3.1–3.4 (m, 1H), 3.59 (s, 3H), 3.9–4.3 (m, 1H), 5.1–5.5 (m, 2H), 6.61 (td, 1H, J=7.5, 2.0Hz).

1 3 g (2.8 mmoles) of 4-(1-octenyl)-5-(6a methoxycarbonylhexylibene -3-(t-butyldimethylsilyloxy)cyclopentanone was dissolved in 40 ml of a solvent consisting of acetic acid, tetrahydrofuran and water in a ratio of 2:1:1, and the solution was stirred at 60° C. for 15 hours. Toluene was added, and the mixture was concentrated under reduced pressure. A saturated aqueous solution of sodium bicarbonate was added. The mixture was extracted with ethyl acetate three times. The organic layers were combined, washed with a saturated aqueous solution of sodium chloride and dried over anhydrous magnesium sulfate. The dried product was filtered, concentrated and subjected to silica gel column chromatography (silica gel 60 g; eluent, hexane:ethyl acetate=7:1 →1:1) to give 32 mg (yield 3%) of 4-(1-octenyl)-5-(6-methoxy-carbonylhexylidene)-2-cyclopentanone, a less polar isomer, and 635 mg (yield 70%) of 4-(1-octenyl)-5-(6-methoxycarbonylhexylidene)-2-cyclopentenone, a more polar isomer.

Spectral data of the less polar isomer:

TLC: Rf=0.33 (hexane:ethyl acetate=5:1)

NMR ($CDCl_3$)δ: 0.85 (brt, 3H, J=4.7 Hz), 1.0–2.5 (m, 18H), 2.5–3.0 (m, 2H), 3.58 (s, 3H), 3.5–4.0 (m, 1H), 5.10 (dd, 1H, J=15.6, 8.0 Hz), 5.48 (dd, 1H, J=15.6, 6.0 Hz), 5.88 (brt, 1H, J=7.2 Hz), 6.16 (dd, 1H, J=6.0, 2.2 Hz), 7.18 (dd, 1H, J=6.0, 2.4 Hz).

Spectral data of the more polar isomer:

TLC: Rf=0.25 (hexane:ethyl acetate=5:1)

NMR(CDCl3) δ: 0.85 (brt, 3H, J=4.2 Hz), 1.0–2.5 (m, 20H), 3.58 (s, 3H0, 3.7–4.1 (m, 1H), 5.12 (dd, 1H, J=15.0, 7.7 Hz)m, 5.52 (dt, 1H, J=15.0, 6.2 Hz), 6.19 (dd, 1H, J=5.8, 1.0 Hz), 6.49 (brt, 1H, J=7.8 Hz), 7.24 (dd, 1H, J=6.2, 2.2 Hz).

EXAMPLE 6

Synthesis of 4 butyl-5-(6-methoxycarbonylhexylidene)-3-hydroxycyclopentanone By using 4-butyl-5-(6-methoxycarbonyl-1-hydroxyhexyl)-3-t-butyldimethylsilyloxycyclopentanone, 4-butyl-5-(6-methoxycarbonylhexylidene)-3-hydroxycyclopentanone was prepared in the same way as in Example 1. The resulting product had the following spectral data.

IR (liquid film): 3450, 1735, 1718, 1641 cm$^{-1}$.

NMR (CDCl$_3$)δ: 0.89 (brt, 3H, J=5.0 Hz), 1.0–2.7 (m, 18H), 2.7–3.3 (m, 2H), 3.64 (s, 3H), 4.0–4.3 (m, 1H), 6.68 (dt, 1H, J=7.5, 2.0 Hz).

EXAMPLE 7

Synthesis of 4-butyl-5-(6-methoxycarbonylhexylidene)-2-cyclopentenone 81 mg (0.28 mmole) of 4-butyl-5-(6-methoxy- carbonylhexylidene)-3-hydroxycyclopentanone obtained in Example 6 was disolved in a mixture consisting of 2 ml of acetic acid, 1 ml of tetrahydrofuran and 1 ml of water, and the solution was stirred at 60° C. for 7 hours and then at 90° C. for 50 hours. After the reaction, the reaction mixture was concentrated under reduced pressure and neutralized with an aqueous solution of sodium bicarbonate. The mixture was extracted with ethyl acetate. The organic layer separated was washed with a saturated aqueous solution of sodium chloride, and dried over anhydrous magnesium syulfate. The dried product was filtered, concentrated and purified by silica gel column chromatography (silica gel 10 g; hexane:ethyl acetate=6:1) to give 61 mg (0.22 mmole; 81%) of 4-butyl-5-(6-methoxycarbonlhexylidene)-2-cyclopentenone. The resulting compound had the following spectral data.

IR (liquid film): 1739, 1703, 1656, 1580 cm$^{-1}$.

NMR (CDCl$_3$:67 (ppm)): 0.89 (3H, t), 1.0–2.0 (12H, m), 2.0–2.6 (4H, m), 3.3–3.8 (1H, m), 3.67 (3H, s) 6.35 (1H, dd, J=6.0, 2.0 Hz), 6.56 (1H, t), 7.59 (1H, dd, J=6.0, 3.0 Hz).

EXAMPLE 8

Synthesis of 4-octyl-5-(6-carboxyhexylidene)-3-hydroxycyclopentanone

By using 4-octyl-5-(6-carboxyl-1-hydroxyhexyl)-3-t-butyldimethylsilyloxycyclopentanone, 4-octyl-5-(6-carboxyhexylidene)-3-hydroxycyclopentanone was prepared in the same way as in Example 1. The resulting compound had the following spectral data.

IR (liquid film): 3430, 1738, 1720, 1638 cm$^{-1}$.

NMR (CDCl$_3$)δ: 0.84 (brt, 3H, J=4.7 Hz), 1.0–2.6 (m, 22H), 3.2–3.7 (m, 2H), 3.57 (s, 3H), 4.0–4.3 (m, 1H), 5.2–5.5 (m, 2H), 6.62 (dd, 1H, J=7.4, 2.0 Hz)

EXAMPLE 9

Synthesism of 4-octyl-5-(6-carboxyhexylidene)-2-cyclopentanone 169 mg (0.5 mmole) of 4-octyl-5-(6-carboxyhexylidene)-3-hydroxycyclopentanone was dissolved in 3 ml of tetrahydrofuran, and ml of 0.5N hydrochloric acid was added. The mixture was stirred at room temperature for 4 days. A saturated aqueous solution of sodium chloride was added, and the mixture was extracted with ethyl acetate. The organic layer was washed with a saturated aqueous solution of sodium chloride, and dried over anhydrous magnesium sulfate. The dried product was filtered, concentrated, and purified by preparative silica gel-thin-layer chromatography to give 12 mg (0.35 mmole; yield 70%) of 4-octyl-5-(6-carboxyhexylidene)-2-cyclopentanone. The resulting compound had the following spectral data.

IR (CHCl$_3$ solution): 20 3650–2400, 1700, 1646, 1580 cm$^{-1}$.

NMR (CDCl$_3$: δ(ppm)): 0.89 (t, 3H), 1.0–2.0 (m, 20H), 2.0–2.6 (m, 4H), 3.3–3.8 (m, 1H), 6.33 (dd, 1H, J=6.2 Hz), 6.60 (t, 1H), 7.53 (dd, 1H, J=6.3 Hz), 11.5 (1H).

EXAMPLE 10

Synthesis of 4-butyl-5-(6-methoxycarbonyl)-2-hexynylidene)-3-hydroxycyclopentanone By using 4-butyl-5-(6-methoxycarbonyl-1-hydroxy-2-hexynyl)-3-t-butyldimethylsilyloxycyclopentanone, 4-butyl-5-(6-methoxycarbonyl-2-hexynylidene)-3-hydroxycyclopentanone was prepared in the same way as in Example 1. The resulting compound had the following spectral data.

IR (liquid film): 3440, 2200, 1735, 1715, 1608 cm$^{-1}$.

NMR (CDCl$_3$) δ: 0.85 (brt, 3H, J=4.5 Hz), 1.0–2.7 (m, 14H), 2.7–3.3 (m, 2H), 3.64 (s, 3H), 4.0–4.3 (m, 1H), 6.3–6.5 (m, 1H)

EXAMPLE 11

Synthesis of 4-butyl-5-(6-methoxycarbonyl-2-hexynylidene)-2-cyclopentenone 29 mg (0.1 mmole) of 4-butyl-5-(6-methoxycarbonyl-2-hexynylidene)-3-hydroxycyclopentanone was dissolved in a mixture of 1 ml of acetic acid, 0.5 ml of tetrahydrofuran and 0.5 ml of water and the solution was stirred at 50° C. for 18 hours in the same way as in Example 1. The reaction mixture was worked up and separated in the same way as in Example 7 to give 13 mg (0.047 mmole; 47% yield) of 4-butyl-5-(6-methoxycarbonyl-2-hexynylidene)-2-cyclopentenone. The resulting compound had the following spectral data.

IR (liquid film): 2190, 1730, 1680, 1620, 1565 cxm$^{-1}$.

NMR (CDCl$_3$: δ(ppm)): 0.88 (3H, t), 1.0–2.2 (8H, m), 2.2 2.8 (4H, m), 3.3–3.8 (1H, m), 3.67 (3H, s), 6.40 (1H, dd, J=6.0, 2.0 Hz), 6.55 (1H), 7.53 (1H, dd, J=6.0, 3.0 Hz).

EXAMPLE 12

Synthesis of 4-(3-t-butyldimethylsilyloxy-3-cyclopentyl-1-propenyl)-5-(6-methoxycarbonyl-2-hexynylidene)-3-t-butyldimethylsilyloxycyclopentanone By using 4-(3-t-butyldimethylsilyloxy)-3-cyclopentyl-1-propenyl-5-(6-methoxycarbonyl 1-hydroxy-2-hexynylidene)-3-t-butyldimethylsilyloxycyclopentanone, 4-(3-t-butyldimethylsilyloxy-3-cyclopentyl-1-propenyl)-5-(6-methoxycarbonyl-2-hexylidene)-3-t-butyldimethylsilyloxycyclopentanone was prepared in the same way as in Example 1. The spectral data of the resulting compound were as follows:

IR: 2218, 1749, 1730, 1620, 1254, 833, 771 cm$^{-1}$.

NMR (CDCl$_3$, δ(ppm)): 0–0.2 (m, 12H), 0.89 (s, 18H), 1.1–2.5 (m, 17H), 3.3–3.65 (m, 1H), 3.67 (s, 3H), 3.75–4.5 (m, 2H), 5.4–5.9 (m, 2H), 6.4–6.7 (m, 1H).

EXAMPLE 13

Synthesis of 4-(3-hydroxy-3-cyclopentyl-1-propenyl)-5-(6-methoxycarbonyl-2-hexynyliodene)-2-cyclopentenone 48 mg (81 micromoles) of 3-t-butyldimethylsilyloxy-4-(3-t-butyldimethylsilyloxy-3-cyclopentyl-1-propenyl)-5-(6-methoxycarbonyl-2-hexylidene)cyclopentanone was dissolved in a mixture of 1.5 ml of acetic acid, 1 ml of tetrahydrofuran and 1 ml of water, and the solution was stirred at 40° C. for 35 hours. [In the early stage of the reaction, 3-hydoxy-4-(3-hydroxy-3-cyclopentyl-1-propenyl)-5-(6-methoxycarbonyl-2-hexynylidene)cyclopentanone formed. This was confirmed from the fact that it agreed in thin-layer chromatography with a separately prepared sample.] After the reaction, the reaction mixture was concentrated under reduced pressure and neutralized with sodium bicarbonate. The mixture was extracted with ethyl acetate. The organic layer separated with a saturated aqueous solution of sodium chloride, and dried over anhydrous magnesium sulfate. The dried product was filtered, concentrated, and purified by silica gel column chromatography (silica gel 3 g; hexane:ethyl acetate=3:1) to give 19 mg (55 micromoles; yield 69%) of 4-(3-hydroxy-3-cyclopentyl-1-propenyl)-5-(6-methoxycarbonyl-2-hexynylidene-2-cyclopentanone. cyclopentanone. The resulting compound had the following spectral data.

IR (liquid film): 3450, 2190, 1728, 1683, 1620, 1565, 743 cm$^{-1}$.

NMR (CDCl$_3$: δ(ppm)): 0.9–2.3 (m, 11H), 2.3–2.8 (m, 5H), 3.70 (s, 3H), 3.45–4.35 (m, 2H), 5.5–5.9 (m, 2H), 6.3–6.7 (m, 2H), 7.4–7.7 (m, 1H).

EXAMPLE 14

Synthesis of 7(E)-7,8-dehydro-17(S),20-dimethylprostaglandin A$_1$ methyl ester In the same way as in Example 13, 7(E)-7,8-dehydro-17(S),20-dimethylprostaglandin A$_1$ methyl ester was obtained from 7(E)-7,8-dehydro-17(S),20-dimethylprostaglandin E$_1$ methyl ester-11,15-bis-t-butyldimethylsilyl ester.

NMR (CDCl$_3$: δ(ppm)): 0.8–1.0 (m, 6H), 1.0–2.0 (m, 15H), 2.0–2.6 (m, 4H), 3.65 (s, 3H), 4.15 (m, 3H), 5.4 (dd, 1H, J=15.6 Hz), 5.75 (dd, 1H, J=15.6 Hz), 6.35 (dd, 1H, J=6.2 Hz), 6.6 (t, 1H, J=6 Hz), 7.4 (dd, 1H, J=6.2 Hz).

EXAMPLE 15

Synthesis of 3-n-butyl-4-t-butyldimethylsilyloxy-2-(1-hydroxybutyl)cyclopentanone and 4-n-butyl-5-(1-hydroxybutyl)-2-cyclopentenone (1) 390 mg (2.05 mmoles) of cuprous iodide was taken into reaction vessel. The reaction vessel was purged with argon, and 20 ml of dry ether and 1.02 ml (4.1 mmoles) of tributyl phosphine were added. The mixture was stirred for 10 minutes. The mixture was cooled to −78° C., and 1.25 ml (0.05 mmoles) of n-butyllithium (as a 1.64M hexane solution) was added, and the mixture was stirred for 5 minutes. The solution of 425 mg (2.0 mmoles) of 4-t-butyldimethylsilyloxy-2-cyclopentenone in 5 ml of dry ether was added to the mixture, and the mixture was stirred at −78° C. for 10 minutes and then at −40° C. for 20 minutes. A solution of 148 mg (2.05 mmoles) of butanal in 5 ml of dry ether was added, and the mixture was stirred at −40° C. for 1 hour. A saturated aqueous solution of ammonium chlorde (50 ml) was added, and the mixture was extracted with ether. The etheric layers were combined and dried over anhydrous magnesium sulfate. The dried product was filtered, concentrated, and subjected to silica gel column chromatography (silica gel, 50 g, eluent, benzene:ethyl acetate=10:1→3:1) to give 329 mg (yield 48%) of 3-n-butyl-4-butyldimethylsilyloxy-2-(1-hydroxybutyl)cyclopentanone.

The resulting product had the following spectral data.

IR (liquid film): 3450, 1735, 1250 cm$^{-1}$.

NMR (CDCl$_3$)δ: 0–0.2 (m, 6H), 0.7–1.1 (m, 6H), 0.89 (s, 9H), 1.1–3.0 (m, 15H), 3.6–4.5 (m, 2H).

(2) 137 mg (0.4 mmole) of 3-n-butyl-4-t-butyl-dimethylsilyloxy-2-(1-hydroxybutyl)cyclopentanone obtained in (1) above was dissolved in a mixture of acetica acid, tetrahydrofuran and water in a ratio of 2:1:1, and the solution was refluxed at 70° C. for 15 hours. Water and sodium bicarbonate were added to render the reaction mixture basic, and it was extracted with ethyl acetate. The organic layers were combined, washed with a saturated aqueous solution of sodium chloride and dried over anhydrous magnesium sulfate. The dried product was filtered, concentrated, and subjected to silica gel column chromatography (silica gel, 5 g; eluent, hexane:ethyl acetate=5:1→ 1:1) to give 61 mg (yield 73%) of 4-n-butyl-5-(1-hydroxybutyl)-2-cyclopentenone. The spectral data of the resulting compound were as follows:

IR (liquid film): 3480, 1698, 1585 cm$^{-1}$.

NMR (CDCl$_3$)δ: 0.7–1.1 (m, 6H), 1.1–3.0 (m, 13H), 3.7–4.1 (m, 1H), 6.22 (dd, 1H, J-5.8, 2.4 Hz), 7.81 (dd, 1H, J=5.8 m 2.8 Hz).

EXAMPLES 16 TO 19

(1) In the same way as in Example 15, (1) the 3-alkyl-4-t-butyldimethylsilyloxy-2-(1-hydroxyalkyl)cyclopentanones shown in Table 1 were obtained.

TABLE 1

| Example | Compound obtained | Yield (%) | IR (cm$^{-1}$) | NMR (CDCl$_3$)δ |
|---|---|---|---|---|
| 16 | 3-n-Butyl-4-t-butyldimethylsilyloxy-2-(1-hydroxy-2-methylpropyl)cyclopentanone | 64 | 3470 1735 1252 | 0–0.2 (m, 6H), 0.7–1.1 (m, 9H), 0.89 (s, 9H), 1.1–1.9 (m, 12H), 3.3–3.6 (m, 1H), 3.9–4.5 (m, 1H), |
| 17 | 3-n-Butyl-4-t-butyldimethylsilyloxy-2-(1-hydroxy-2,2-dimethylpropyl)cyclopentanone | 34 | 3490 1731 1250 | 0–0.2 (m, 6H), 0.7–1.1 (m, 3H), 0.89 (s, 18H), 1.1–2.7 (m, 11H), 3.1–3.5 (m, 1H), 4.3–4.7 (m, 1H) |

TABLE 1-continued

| Example | Compound obtained | Yield (%) | IR (cm⁻¹) | NMR (CDCl₃)δ |
|---|---|---|---|---|
| 18 | 3-n-Butyl-4-t-butyldimethylsilyl-oxy-2-(1-hydroxy-3-phenyl-2-propen-1-yl)cyclopentanone | 45 | 3480<br>1723<br>1251<br>962 | 0–0.2 (m, 6H), 0.7–1.1 (m, 3H),<br>0.89 (s, 9H), 1.1–2.8 (m, 10H),<br>3.3–3.6 (m, 1H), 4.2–4.8 (m, 2H),<br>6.32 (dd, 1H, J=16.0, 6.8Hz),<br>6.60 (d, 1H, J=16.0Hz),<br>7.0–7.6 (m, 5H) |
| 19 | 3-t-Butyl-4-t-butyldimethylsilyl oxy-2-(1-hydroxybutyl)cyclo-pentanone | 37 | 3490<br>1738<br>1249 | 0–0.2 (m, 6H), 0.7–1.1 (m, 3H),<br>0.90 (s, 18H), 1.1–2.7 (m, 9H),<br>3.3–3.6 (m, 1H), 4.0–4.5 (m, 1H) |

(2) In the same way as in Example 15, (2) the 4-alkyl-5-(1-hydroxyalkyl)2-cyclopentenones indicated in Table 2 were obtained from the 3-alkyl-4-t-butyl-dimethylsilyloxy-2-(1-hydroxyalkyl)cyclopentenones obtained in (1) above. The results are shown in Table 2.

TABLE 2

| Example | Compound obtained | Yield (%) | IR (cm⁻¹) | NMR (CDCl₃)δ |
|---|---|---|---|---|
| 16 | 4-n-Butyl-5-(1-hydroxy-2-methyl-propyl)-2-cyclopentenone | 63 | 3510<br>1700<br>1580 | 0.7–1.1 (m, 9H), 1.1–3.1 (m, 10H),<br>3.4–3.8 (m, 1H), 6.20 (dd, 1H,<br>J=5.8, 2.5Hz), 7.80 (dd, 1H,<br>J=5.8, 2.8Hz) |
| 17 | 4-n-Butyl-5-(1-hydroxy-2,2-dimethylpropyl)-2-cyclopentenone | 41 | 3495<br>1696<br>1590 | 0.7–1.1 (m, 3H), 1.1–3.1 (m, 9H),<br>3.1–3.6 (m, 1H), 6.21 (dd, 1H,<br>J=5.9, 2.6Hz), 7.80 (dd, 1H,<br>J=5.9, 2.8Hz) |
| 18 | 4-n-Butyl-5-(1-hydroxy-3-phenyl-2-propen-1-yl)-2-cyclopentenone | 46 | 3490<br>1697<br>1595<br>960 | 0.7–1.1 (m, 3H), 1.1–3.4 (m, 7H),<br>3.3–3.6 (m, 1H), 4.3–4.7 (m, 1H),<br>6.0–6.8 (m, 3H), 7.0–8.0 (m, 6H) |
| 19 | 4-t-Butyl-5-(1-hydroxybutyl)-2-cyclopentenone | 40 | 3500<br>1701<br>1585 | 0.7–1.1 (m, 3H), 0.90 (s, 9H),<br>1.1–3.0 (m, 7H), 3.6–4.0 (m, 1H),<br>6.25 (dd, 1H, J=6.0, 2.6Hz),<br>7.75 (dd, 1H, J=6.0, 2.8Hz) |

EXAMPLE 20

Synthesis of 3-n-butyl-4-t-butyldimethylsilyloxy-2-(1-hydroxy-6-methoxycarbonylhexyl)cyclopentanone and 4-n-butyl-5-(1-hydroxy-6-methoxycarbonylhexyl)-2-cyclopentenone (1) 6.2 ml (20 mmoles) of hexamethylphosphoric triamide was added to 1.88 g (14.4 mmoles) of 1-pentynyl copper, and the mixture was stirred for 30 minutes. Then, 50 ml of dry ether was added, and the mixture was cooled to −78° C. 9.6 ml (14.4 mmoles) of n-butyllithium (1.5M hexane solution) was added, and the mixture was stirred for 15 minutes. A solution of 2.55 g (12 mmoles) of 4-t-butyldimethylsilyl-2-cyclopentenone in 30 ml of dry ether was added. and the mixture was stirred at −40° C. for 15 minutes. A solution of 2.28 g (14.4 mmoles) of methyl 7-oxoheptanoate in 30 ml of dry ether was added, and the mixture was stirred at −40° C. for 1 hour. A saturated aqueous solution of ammonium chloride and ammonia and hexane were added to extract the reaction mixture. The organic layer was washed with a saturated aqueous solution of ammonium chloride and then with a saturated aqueous solution of sodium chloride, and dried over anhydrous magnesium sulfate. The dried product was filtered, concentrated and subjected to silica gel column chromatography (silica gel 100 g; eluent, hexane:ethyl acetate=8:1→2:1) to give 0.55 g (yield 11%) of 3-n-butyl-4-butyldimethylsilyloxy-2-(1-hydroxy-6-methoxycarbonylhexyl)cyclopentanone. The resulting compound had the following spectral data.

none was obtained in a yield of 73% from 3-n-butyl-4-t-butyldimethylsilyloxy-2-(1-hydroxy-6-methoxycarbonylhexyl)cyclopentanone obtained in (1) above. The resulting compound had the following spectral data.

IR (liquid film): 3480, 1737, 1698, 1585 cm⁻¹.

NMR (CDCl₃)δ: 0.7–1.1 (m, 3H), 1.1–3.0 (m, 20H), 3.70 (s, 3H), 3.7–4.1 (m, 1H), 6.21 (dd, 1H, J=5.8, 2.4 Hz), 7.81 (dd, 1H, J=5.8, 12.8 Hz).

EXAMPLE 21

Synthesis of 3-(2-propenyl)-4-t-butyldimethylsilyloxy-2-(1-hydroxybutyl)cyclopentanone and 4-(2-propenyl)-5-(1-hydroxybutyl)-2-cyclopentenone (1) 266 mg (2.2 mmoles) of 2-bromopropene was dissolved in 5 ml of dry ether, and the solution was cooled to −95° C. Then, 3.0 ml (4.8 mmoles) of t-butyllithium (as 1.60M pentane solution) was added, and the mixture was stirred at −78° C. for 2 hours to form a 2-propenyllithium solution. 300 mg (2.05 mmoles) of cuprous iodide was taken into a reaction vessel. The reaction vessel was purged with argon, and 30 ml of dry ether and 1.02 ml (4.1 mmoles) of tributyl phosphine were added. The mixture was stirred for 10 minutes. The mixture was added to the 2-propenyllithium solution prepared above, and the mixture was stirred for 5 minutes. A solution of 425 mg (2.0 mmoles) of 4-t-butyl-dimethylsilyloxy-2-cyclopentenone in 5 ml of dry ether was added. The mixture was stirred at −78° C. for 10 minutes and −40° C. for 20 minutes. A solution of 148 mg (2.05 mmoles) of butanal in 5 ml of dry ether was added, and the mixture was stirred at −40° C. for 1

IR (liquid film): 3500, 1740, 1250 cm⁻¹.

NMR (CDCl₃)δ: 0–0.2 (m, 6H), 0.7–1.1 (m, 3H), 0.89 (s, 9H), 1.1–2.8 (m, 21H), 3.70 (s, 3H), 3.7–4.4 (m, 2H).

(2) In the same way as in Example 15, (2) 4-n-(2-hydroxy-6-methoxycarbonylhexyl)-2-cyclo-butylpentehour. 50 ml of a saturated aqueous solution of ammonium chloride was added, and the mixture was extracted with ether. The etheric layers were combined, dried over anhydrous magnesium sulfate, filtered, concentrated and then subjected to silica gel column chromatography (silica gel 50 g; eluent, benzene:ethyl acetate=10:1→3:1 to give 287 mg (yield 44%) of 3-(2-propenyl)-4-t-butyldimethylsilyloxy-2-(1-hydroxybutyl)cyclopentanone. The resulting compound had the following spectral data.

IR (liquid film): 3480, 1737, 1640, 1251 cm$^{-1}$.

NMR (CDCl$_3$)δ: 0–0.2 (m, 6H), 0.7–1.1 (m, 3H), 0.90 (s, 3H), 1.1–3.3 (m, 12H), 3.6–4.5 (m, 2H).

(2) In the same way as in Example 15, (2) 4-(2-propenyl)-5-(1-hydroxybutyl)-2-cyclopentenone was obtained from 3-(2-propenyl)-4-t-butyldimethylsilyloxy-2-(1-hydroxybutyl)cyclopentanone obtained in (1) above. The resulting compound had the following spectral data.

IR (liquid film): 3490, 1696, 1637, 1586 cxm$^{-1}$.

NMR (CDCl$_3$)δ: 0.7–1.1 (m, 3H), 1.1–2.8 (m, 9H), 3.0–3.5 (m, 1H), 3.7–4.1 (m, 1H), 6.22 (dd, 1H, J=5.8, 2.3 Hz), 7.79 (dd, 1H, J=5.8, 2.8 Hz).

EXAMPLE 22

Synthesis of 4-t-butyldimethylsilyloxy-3-(3-t-butyldimethylsilyloxy-1-octenyl)-2-(1-hydroxy-6-methoxycarbonylhexyl)cyclopentanone and 4-(3-hydroxy-1-octenyl)-5-(1-hydroxy-6-methoxycarbonylhexyl)-2-cyclopentenone (1) 12 ml (24 mmoles) of t-butyllithium (2.0M pentane solution was cooled to −78° C., and 40 ml of dry ether was added. A solution of 4.42 g of 1-iodo-3-t-butyldimethylsilyloxy-1-octene in 40 ml of dry ether, and the mixture was stirred at −78° C. for 2 hours. A solution prepared by dissolving 1.566 g (12 mmoles) of 1-pentynyl copper (1) in 6.2 ml (29 mmoles) of hexamethylphsophoric triamide and adding 20 ml of dry ether was added and the mixture was stirred at −78° C. for 10 minutes. A solution of 2.12 g (10 mmoles) of 4-t-butyldimethylsilyloxy-2-cyclopentenone in 20 ml of dry ether was added. The mixture was stirred at −78° C. for 5 minutes at −40° C. for 1 hour. The reaction mixture was poured into an acetic acid-sodium acetate buffer (pH 4), and hexane was added to perform extraction. The organic layer was washed with a saturated aqueous solution of sodium chloride, and dried over anhydrous magnesium sulfate. The dried product was filtered, concentrated, and subjected to silica gel column chromatography (silica gel, 200 g; eluent, hexane:ethyl acetate=10:1→2:1 to give 3.19 g (yuield 52%) of 4-t-butyldimethylsilyloxy-3-(t-butyldimethylsilyloxy-1-octenyl)-2-(1-hydroxy-6-methoxycarbonylhexyl)cyclopentanone. The resulting compound had the following spectral data.

IR (liquid film): 3470, 1741, 1251 cm$^{-1}$.

NMR (CDCl$_3$)δ: 0–0.2 (m, 12H), 0.7–1.1 (m, 3H), 0.90 (s, 18H), 1.1–3.0 (m, 23H), 3.69 (s, 3H), 3.6–4.6 (m, 3H), 5.4–5.8 (m, 2H).

(2) 1.23 g (2.0 mmoles) of 4-t-butyldimethylsilyloxy-3-(3-t-butyldimethylsilyloxy-1-octenyl)-2-(1-hydroxy-6-methoxycarbonylhexyl)cyclopentanone obtained in (1) above was dissolved in 10 ml of a hydrogen fluoride-acetonitrile solution (composed of 47% hydrochloric acid and acetonitrile in a ratio of 1:20), and the solution was stirred for 30 minutes. Sodium bicarbonate and water were added, and the mixture was extracted with ethyl acetate. The organic layer was washed with a saturated aqueous solution of sodium chloride, and dried over anhydrous magnesium sulfate. The dried product was filtered, concentrated, and subjected to silica gel column chromatography (silica gel 20 g; eluent, hexane:ethyl acetate=2:1→1:4) to give 577 mg of 4-hydroxy-3-(3-hydroxy-1-octenyl)-2-(1-hydroxy-6-methoxycarbonylhexyl)cyclopentanone. This compound was further dissolved in 10 ml of a mixed solvent composed of acetic acid, tetrahydrofuran and water in a ratio of 2:1:1, and the solution was stirred at 70° C. for 6 hours. An aqueous solution of sodium bicarbonate and ethyl acetate were added to perform extraction. The organic layers were combined, washed with a saturated aqueous solution of sodium chloride, and dried over anhydrous magnesium chloride. The dried product was filtered, concentrated, and subjected to silica gel column chromatography (silica gel, 15 g; eluent, hexane:ethyl acetate=5:1→1:2) to give 352 mg (yield 48%) of 4-(3-hydroxy-1-octenyl)-2-(1-hydroxy-6-methoxycarbonylhexyl)-2-cyclopentenone. The product had the following spectral data.

IR (liquid film): 3470, 1703, 1586 cm$^{-1}$.

NMR (CDCl$_3$)δ: 0.7–1.1 (m, 3H), 1.1–2.9 (m, 21H), 2.9–3.4 (m, 1H), 3.69 (s, 3H), 3.5–4.6 (m, 2H), 5.5–5.9 (m, 2H), 6.24 (dd, 1H, J=5.8, 2.1 Hz), 7.63 (dd, 1H. J=5.8, 2.4 Hz).

EXAMPLE 23

43 mg (0.11 mmole) of 4-hydroxy-3-(3-hydroxy-1-octenyl)-2-(1-hydroxy-6-methoxycarbonylhexyl)cyclopentanone obtained as a reaction intermediate in Example 22, (2) was dissolved in 1.5 ml of tetrahydrofuran, and 1.0 ml of 0.5N hydrochloric acid was added. The mixture was stirred at 40° C. for 3 hours. An aqueous solution of sodium bicarbonate and ethyl acetate were added to perform extraction. The organic layer was washed with a saturated aqueous solution of sodium chloride, and dried over anhydrous magnesium sulfate. The dried product was filtered, concentrated, and subjected to silica gel column chromatography (silica gel, 2 g; eluent, hexane:ethyl acetate=5:1→1:2) to give 21 mg (yield 51%) of 4-(3-hydroxy-1-octenyl)-5-(1-hydroxy-6-methoxycarbonylhexyl)-2-cyclopentenone.

EXAMPLE 24

370 mg (60 mmoles) of 4-t-butyldimethyl silyloxy-3-(3-t-butyldimethylsilyloxy-1-octenyl)-2-(1-hydroxy-6-methoxycarbonylhexyl)cyclopentanone obtained in Example 22, (1) was dissolved in 10 ml of a mixed solvent consisting of acetic acid, tetrahydrofuran and water in a ratio of 2:1:1, and the solution was stirred at 80° C. for 7 hours. An aqueous solution of sodium bicarbonate and ethyl acetate were added to perform extraction. The organic layers were combined, washed with a saturated aqueous solution of sodium chloride, and dried over anhydrous magnesium sulfate. The dried product was filtered, concentratd, and subjected to silica gel column chromatography (silica gel), 10 g; eluent, hexane:ethyl acetate=5:1→1:2) to give 218 mg (yield 62%) of 4-(3-hydroxy-1-octenyl)-5-(1-hydroxy-6-methoxycarbonylhexyl)cyclopentenone.

EXAMPLES 25 TO 27

In the same way as in Example 15, the 3-alkenyl-4t-butyldimethylsilyloxy-2-(1-hydroxyalkyl)cyclopentanones shown in Table 3 and the 4-alkenyl-5-(1-hydroxyalkyl)-2-cyclopentenones in Table 4 were obtained.

posed of acetic acid, tetrahydrofuran and water in a ratio of 3:2:2, and the solution was stirred for 20 hours.

TABLE 3

| Example | Compound obtained | Yield (%) | IR (cm⁻¹) | NMR (CDCl₃)δ |
|---|---|---|---|---|
| 25 | 4-t-Butyldimethylsilyloxy-3-(3-t-butyldimethylsilyloxy-3-cyclopentyl-1-propenyl)-2-(1-hydroxy-6-methoxycarbonyl-2-hexyn-1-yl)-cyclopentanone | 45 | 3470 2230 1738 1252 | 0–0.2 (m, 12H), 0.89 (s, 18H), 1.2–3.0 (m, 20H), 3.70 (s, 3H), 3.5–4.5 (m, 2H), 4.6–5.0 (m, 1H), 5.5–5.8 (m, 2H) |
| 26 | 4-(2-Tetrahydropranyloxy)-3-[3-(2-tetrahydropyranyloxy)-1-octenyl]-2-(1-hydroxy-6-methoxycarbonyl-2-hexyn-1-yl)cyclopentanone | 15 | 3510 2230 1736 | 0.7–1.1 (m, 3H), 1.1–3.0 (m, 31H), 3.3–4.5 (m, 6H), 3.68 (s, 3H), 4.5–5.1 (m, 3H), 5.4–5.8 (m, 2H) |
| 27 | 4-t-Butyldimethylsilyloxy-3-(3-t-butyldimethylsilyloxy-5-methyl-1-nonenyl)-2-(1-hydroxy-6-methoxycarbonyl-5-hexen-1-yl)-cyclopentanone | 42 | 3490 1735 1250 | 0–0.2 (m, 12H), 0.90 (s, 18H), 0.7–1.1 (m, 6H), 1.1–3.2 (m, 20H), 3.71 (s, 3H), 3.3–4.7 (m, 3H), 5.3–5.8 (m, 2H), 5.85 (brd, 1H, 16Hz), 7.03 (dt, 1H, J=16.0, 6.8Hz) |

TABLE 4

| Example | Compound obtained | Yield (%) | IR (cm⁻¹) | NMR (CDCl₃)δ |
|---|---|---|---|---|
| 25 | 4-(3-t-Butyldimethylsilyloxy-3-cyclopentyl-1-propenyl)-5-(1-hydroxy-6-methoxycarbonyl-2-hexyn-1-yl)-2-cyclopentenone | 26 | 3450 2230 1735 1708 1580 1247 | 0–0.2 (m, 6H), 0.89 (s, 9H), 1.2–2.7 (m, 18H), 3.1–3.5 (m, 1H), 3.68 (s, 3H), 3.7–4.1 (m, 1H), 4.6–5.0 (m, 1H), 5.5–5.8 (m, 2H), 6.22 (dd, 1H, J-5.8, 2.0Hz), 7.68 (dd, 1H, J=5.8, 3.2Hz) |
| 26 | 4-[3-(2-tetrahydropyranyloxy)-1-octenyl]-5-(1-hydroxy-6-methoxycarbonyl-2-hexyn-1-yl)-2-cyclopentenone | 36 | 3480 2230 1735 1706 1577 | 0.7–1.1 (m, 3H), 1.1–2.8 (m, 22H), 3.0–4.4 (m, 4H), 3.70 (s, 3H), 4.5–5.0 (m, 2H), 5.4–5.7 (m, 2H), 6.21 (dd, 1H, J=5.7, 2.0Hz), 7.67 (dd, 1H, J=5.7, 2.2Hz) |
| 27 | 4-(3-t-Butyldimethylsilyloxy-5-methyl-1-nonenyl)-5-(1-hydroxy-6-methoxycarbonyl-5-hexen-1-yl)-2-cyclopentenone | 12 | 3510 1734 1704 1250 | 0–0.2 (m, 6H), 0.89 (s, 9H), 0.7–1.1 (m, 6H), 1.1–2.7 (m, 17H), 2.9–3.4 (m, 1H), 3.72 (s, 3H), 3.55–4.6 (m, 2H), 5.5–5.9 (m, 2H), 5,88 (brd, 1H, J=16.0Hz), 6.25 (dd, 1H, J=5.8, 2.0Hz), 7.04 (dt, 1H, J=16.0, 7.2Hz), 7.63 (dd, 1H, J=5.8, 2.4Hz) |

EXAMPLE 28

Synthesis of 4-(3-hydroxy-5-methyl-1-nonenyl)-5-(1-hydroxy-6-methoxyxcarbonyl-5-hexen-1-yl)-2-cyclopentenone In the same way as in Example 22, 6.7 mg (yield 43%) of 4-(3-hydroxy-5-methyl-1-nonenyl)-5-(1-hydroxy-6-methoxycarbonyl-5-hexen-1-yl)-2-cyclopentenone was obtained from 20 mg (0.039 mmmole) of 4-(3-t-butyldimethylsilyloxy-5-methyl-1-nonenyl)-5-(1-hydroxy-6-methoxycarbonyl-5-hexen-1-yl)-2-cyclopentenone obtained in Example 27. The resulting compound had the following spectral data.

IR (liquid film): 3520, 1702, 1580 cm⁻¹.

NMR (CDCl₃)δ: 0.7–1.05 (m, 6H), 1:05–2.0 (m, 13H), 2.0–2.7 (m, 5H), 2.9–3.5 (m, 1H), 3.74 (s, 3H), 3.55–4.6 (m, 2H), 5.5–5.9 (m, 2H), 5.88 (brd, 1H, J=16.0 Hz), 6.26 (dd, 1H, J=5.8, 2,0 Hz), 7.05 (dt, 1H, J=16.0, 7.2 Hz), 7.64 7.64 (dd, 1H, J=5.8, 2.4 Hz).

EXAMPLE 29

Synthesis of 4-(3-hydroxy-3-cyclopentyl-1-propenyl)-5-(1-hydroxy-6-methoxycarbonyl-2-hexyn-1-yl)-2-cyclopentenone 63 mg (0.133 mmole) of 4-(3-t-butyldimethylsilyloxy-3-cyclopentyl-1-propenyl)-5-(1-hydroxy-6-methoxycarbonyl-2-hexyn-1-yl)-2-cyclopentenone obtained in Example 25 was dissolved in 2 ml of a mixed solvent com- An aqueous solution of sodium bicarbonate and ethyl acetate were added to the reaction mixture to perform extraction. The organic layers were combined, washed with a saturated aqueous solution of sodium chloride, and dried over anhydrous sodium sulfate. The dried product was filtered, concentrated and subjected to silica gel column chromatography (silica gel 5 g; eluent, hexane:ethyl acetate=5:1→1:1) to give 38 mg (yield 79%) of 4-(3-hydroxy-3-cyclopentyl-1-propenyl)-5-(1-hydroxy-6-methoxycarbonyl-2-hexyn-yl)-2-cyclopentenone. The resulting compound had the following spectral data.

IR (liquid film): 3450, 2240, 1700, 1583 cm⁻¹.

NMR (CDCl₃)δ: 0.9–2.8 (m, 18H), 3.68 (s, 3H), 3.5–4.3 (m, 3H), 4.6–5.0 (m, 1H), 5.6–6.0 (m, 2H), 6.21 (dd, 1H, J=6.0, 2.0 Hz), 7.71 (dd, 1H), J=6.0, 2.4 Hz).

EXAMPLE 30

Synthesis of 4-(3-hydroxy-1-octenyl)-5-(1-hydroxy-6-carboxyhexyl)-2-cyclopentenone Acetone (0.6 ml) and 6 ml of phosphate buffer (pH 8) were added to 50 mg (0.135 mmole) of 4-(3-hydroxy-1-octenyl)-5-(1-hydroxy-6-methoxy-carbonylhexyl)-2-cyclopentenone obtained in Example 24, and then 0.06 ml of an aqueous solution of esterase (from pig liver) was added. The mixture was stirred for 70 hours. Hydrochloric acid was added to the reaction mixture to adjust its pH to 4, and then the mixture was saturated with ammonium sulfate. It was filtered, and then extracted with ethyl acetate. The organic layer was washed with an aqueous solution of sodium chloride, and dried over anhydrous magnesium sulfate. The dried product was filtered, concentratd and subjected to silica gel column chromatography (silica gel 2 g; eluent, hexane:ethyl acetate=2:1→1:4) to give 31 mg (yield 65%) of 4-(3-hydroxy-1-octenyl)-5-(1-hydroxy-6-carboxyl-hexyl)-2-cyclopentene. The resulting compound had the following spectral data IR (liquid film): 3400, 1702, 1585 cm$^{-1}$.

NMR (CDCl$_3$)δ: 0.7–1.1 (m, 3H), 1.1–2.9 (m, 22H), 2.9–3.4 (m, 1H), 3.5–4.6 (m, 2H), 5.4–5.9 (m, 2H), 6.23 (dd, 1H, J=5.8, 2.1 Hz), 7.63 (dd, 1H, J=5.8, 2.4 Hz)

EXAMPLE 31

Synthesis of 4-(3-t-butyldimethylsilyloxy-1-octenyl)-5-(6-methoxycarbonylhexylidene)-2-cyclopentenone 480 mg (1.0 mmole) of 4-(3-t-butyldimethylsiloxy-1-octenyl)-5-(1-hydroxy-6-methoxycarbonylhexyl)-2-cyclopentenone was dissolved in 5 ml of dichloromethane, followed by addition of 730 mg (6 mmoles) of dimethylaminopyridine and 230 microliters (3.0 mmoles) of methanesulfonyl chloride in this order. The mixture was stirred at 40° C. for 2 hours. An aqueous solution of sodium bicarbonate was added, and the mixture was stirred with dichloromethane. The organic layers were combined, washed with a saturated aqueous solution of sodium chloride and dried over anhydrous sodium sulfate. The dried product was filtered, concentrated and subjected to silica gel column chromatography (silica gel 20 g; eluent, hexane:ethyl acetate=10:1) to give 114 mg (yield 25%) of 4-(3-t-butyldimethylsilyloxy-1-octenyl)-5-(6-methoxycarbonylhexylidene)-2-cyclopentenone. The resulting compound had the following spectral data.

TLC: Rf=0.54 (hexane:ethyl acetate=3:1)

NMR (CDCl$_3$)δ: 0–0.2 (m, 6H), 0.86 (s, 9H), 0.7–1.0 (m, 3H), 1.1–2.0 (m, 14H), 2.0–2.7 (m, 4H), 3.67 (s, 3H), 3.7–4.3 (m, 2H), 5.3–5.8 (m, 2H), 6.36 (dd, 1H, J=6.0, 1.8 Hz), 6.65 (brt, 1H, J=8.0 Hz), 7.45 (dd, 1H, J=6.0, 2.8 Hz).

EXAMPLE 32

Synthesis of 4-butyl-5-(6-methoxycarbonylhexylidene)-2-cyclopentenone 1.7 g (5.74 mmoles) of 4-butyl-5-(1-hydroxy-6-methoxycarbonyl)-2-cyclopentenone was dissolved in 20 ml of dichloromethane, and 3.86 g (31.6 mmoles) of 4-dimethylaminopyridine was added. With ice cooling and stirring, 900 microliters (11.6 mmoles) of methanesulfonyl chloride was added. The mixture was stirred at 0° C. for 10 minutes and then at room temperature for 20 hours. Water and hydrochloric acid was added to adjust the pH of the reaction mixture to 1, and it was extracted with methylene chloride. The organic layer was washed with a saturated aqueous solution of sodium bicarbonate, and dried over anhydrous sodium sulfate. The dried product was filtered, concentrated and subjected to silica gel column chromatography (silica gel, 20 g; eluent, hexane:ethyl acetate=8:1→4:1) to give 111 mg (yield 7%) of 4-butyl-(Z)-5-(6-methoxycarbonylhexylidene)-2-cyclopentenone and 1.363 g (yield 86%) of 4-butyl-(Z)-5-(6-methoxycarbonylhexylidene)-2-cyclopentenone.

Spectral data of 4-butyl-(Z)-5-(6-methoxycarbonylhexylidene)-2-cyclopentenone:

TLC: Rf=0.53 (hexane:ethyl acetate-2:1)

IR(liquid film): 1739, 1694, 1642, 1583 cm$^{-1}$.

NMR (CDCl$_3$)δ: 0.7–1.1 (m, 3H), 1.1–2.0 (m, 12H), 2.0–2.55 (m, 2H), 2.55–3.2 (m, 2H), 3.1–3.5 (m, 1H), 3.69 (s, 3H), 6.07 (brt, 1H, J=7.5 Hz), 6.31 (dd. 1H, J=6.0, 2.0 Hz), 7.50 (dd, 1H, J=6.0, 3.0 Hz).

Spectral data of 4-butyl-(E)-5-(6-methoxycarbonylhexylidene)-2-cyclopentenone:

TLC: Rf=0.42 (hexane:ethyl acetate=2:1)

IR (liquid film): 1739, 1703, 1656, 1580 cm$^{-1}$.

NMR (CDCl$_3$)δ: 0.89 (brt, 3H), 1.0–2.0 (m, 12H), 2.0–2.6 (m, 4H), 3.3–3.8 (m, 1H), 3.67 (s, 3H) 6.35 (dd, 1H, J=6.0, 2.0 Hz), 6.56 (brt, 1H), 7.59 (dd, 1H, J=6.0, 3.0 Hz).

EXAMPLE 33

Synthesis of 4-(1-octenyl)-5-(1-hydroxy-6-methoxycarbonylhexylidene)-2-cyclopentenone In the same way as in Example 15, 4-(1-octenyl)-5-(1-hydroxy-6-methoxycarbonylhexylidene)-2-cyclopentenone was obtained in an amount of 1.32 g (yield 38%). The product had the following spectral data.

TLC: Rf=0.13 (hexane:ethyl acetate=4:1)

NMR (CDCl$_3$)δ: 7.86 (brt, 3H, J=4.5 Hz), 1.0–1.8 (m, 16H), 1.85–2.5 (m, 5H), 3.1–3.4 (m, 1H), 3.64 (s, 3H), 3.4–4.0 (m, 1H), 4.0–4.2 (m, 1H), 7.55 (dd, 1H, J=6.0, 2.4 Hz).

EXAMPLE 34

Synthesis of 4-(1-octenyl)-5-(6-methoxycarbonylhexylidene)-2-cyclopentenone 300 mg (0.86 mmole) of 4-(1-octenyl)-5-(1-hydroxy-6-methoxycarbonylhexyl)-2-cyclopentene obtained in Example 33 was dissolved in 5 ml of anhydrous dichloromethane, and 640 mg (5.2 mmoles) of dimethylaminopyridine and 200 microliters (2.6 mmoles) of methanesulfonyl chloride were added in this order. The mixture was stirred at room temperature for 4 hours, and 50 ml of ether was added. The organic layer was washed with an acetic buffer (pH 4) and then with water and further with an aqueous solution of sodium chloride, and dried. The solvent was evaporated, and the residue was purified by thin-layer chromatography (solvent, hexane:ether=3:1, Rf=0.4, Rf of the starting enone being 0.25) to give 135 mg (yield 48%) of a mixture of isomers of 4-(1-octenyl)-5-(6-methoxycarbonylhexylidene)-2-cyclopentenone of Example 5.

EXAMPLE 35

Measurement of the Action of Inhibiting Proliferation of L1210 Leukemia Cell

L1210 leukemia cells were added to an RPMI medium containing 10% FCS (fetal calf serum), and the concentration of the cells was adjusted to $1 \times 10^5$ cells/ml. Each of the test compounds shown in Table 5 was dissolved in 99.5% ethanol. Prior to use, the final concentration of the ethanol solution was adjusted to less than 0.1%, and it was added to the culture medium. The culture medium was then maintained at 37° C. in a stationary condition for 4 days. After the cultivation, the number of surviving cells was measured by dyeing with trypan blue. As a control, 0.1% ethanol was used. A dose-reaction curve was plotted from the ratios of proliferation against the control, and $IC_{50}$ was determined.

The results are shown in Table 5.

TABLE 5

| Test compound | $IC_{50}$ (μg/ml) |
|---|---|
| 7(E)-7,8-Dehydroprostaglandin $E_1$ | 0.7 |
| 7(E)-7,8-Dehydroprostaglandin $A_1$ | 0.4 |
| 4-Butyl-5-(6-methoxycarbonylhexylidene)-2-cyclopentenone | 0.3 |
| 4-(3-Hydroxy-3-cyclopentyl-1-propenyl)-5-(6-methoxycarbonyl-2-hexynylidene)-2-cyclopentenone | 0.3 |
| 4-(3-Hydroxy-5-methyl-1-nonenyl)-5-(6-methoxycarbonyl-2-hexynylidene)-2-cyclopentenone [7(E)-7,8-dehydro-17(S),20-dimethylprostaglandin $A_1$ methyl ester] | 0.2 |
| 4-(3-Hydroxy-3-cyclopentyl-1-propenyl)-5-(1-hydroxy-6-methoxycarbonyl-2-hexyn-1-yl)-2-cyclopentenone | 0.2 |
| 12-Epi-(7E)-7,8-dehydroprostaglandin $A_1$ methyl ester | 0.2 |
| 4-(1-Octenyl)-5-(6-methoxycarbonyl-hexynylidene)-2-cyclopentenone | 0.3 |

EXAMPLE 36

Measurement of the Antitumor Effect On Ehrich Ascites Carcinoma $1 \times 10^5$ Ehrlich ascites carcinoma cells were intraperitoneally administred to ICR mice. After the lapse of 24 hours, 30 mg/kg/day of 7(E)-7,8-dehydroprostaglandin $A_1$ methyl ester and 20 mg/kg/day of its 12-epimer were each intraperitoneally administered to the mice for 5 days. The periods of survival of these animals were examined.

When 7(E)-7,8-dehydroprostaglandin $A_1$ methyl ester was administered, the average number of days of survival was 31±1.9 days. The increase of life span (ILS %) increased by 65.8% over the control, and the ratio of survival for more than 60 days was 2/6.

In the case of administering its 120 epimer, the average number of days of survival was 33.0±9.8 days. The increase of life span (ILS %) increased by 76.5% over the control, and the ratio of survival fo more than 60 days was 1/6.

EXAMPLE 37

Measurement of Cyto Protection

Stomach epithelial cells taken from a rabbit fetus and aortic smooth muscle cells from a rat were used as normal cells, and L1210 leukemia cells were used as cancer cells. The cytotoxicity of each of the compounds shown in Table 6 on the normal cells was xamined.

Specifically, the stomach epithelial cells were cultivated in DME containing 20% FCS, and the aortic smooth muscle cells were cultivated in MEM containing 10% CS. Each of the test compounds was dissolved in ethanol and added to the culture broth in an amount of 0.1%. The mixture was filtered through a millipore filter.

The cytotoxicities $LD_{50}$) of each of the test compounds on the stomach epithelial cells and the aortic smooth muscle cells were determined. The results are shown in Table 6. Furthermore, from the $LFD_{50}$ values, the safety coefficient ($LD_{50}$ on the normal cells/$LD_{50}$ on the L1210 cells) was calculated, and the results are also shown in Table 6.

TABLE 6

| | $LD_{50}$ (μg/ml) | | | |
|---|---|---|---|---|
| Test compound | Stomach epitherial cells | Aortic smooth muscle cells | L1210 leukemia cells | Safety coefficient |
| 7(E)-7,8-dehydro-prostaglandin $A_1$ | 2–5 | 2–5 | 0.2–0.3 | 6–25 |
| 12-Epimer of 7(E)-7,8-dehydroprostaglandin $A_1$ | 1–2 | 1–2 | 0.2–0.4 | 2.5–10 |
| Comparison (Mytomycin C) | 0.01–0.02 | 0.01 | 0.1 | 0.01–0.1 |

It is seen from Table 6 that the compounds of this invention have low cytotoxicity on normal cells.

EXAMPLE 38

Measurement of Acute Toxicity

The acute toxicity of one typical compound of this invention was measured by a customary method using four weeks old LR strain male mice (SPF).

The results are shown in Table 7.

TABLE 7

| Compound | Administration route | $LD_{50}$ (mg/kg) |
|---|---|---|
| 7(E)-7,8-dehydroprostaglandin $A_1$ | i.v. | 140 |

Table 7 shows that the compound of this invention has low acute toxicity.

EXAMPLE 39

Production of Soft Capsules

One milligrams of (7E)-7,8-dehydro $PGA_1$ obtained in Example 2 was dissolved in 60 g of fractionated coconut oil and soft capsules were produced using a soft gelatin capsule making machine. Each of the capsules containing 1 g of (7E)-7,8-dehydro $PGA_1$.

EXAMPLE 40

Production of Tablets

Tablets were produced each of which contained the following ingredients.

| | |
|---|---|
| 4-(3-hydroxy-3-cyclopentyl-1-propenyl)-5-(1-hydroxy-6-methoxycarbonyl-2-hexyn-1-yl)-2-cyclopentenone | 10 g |
| Lactose | 250 mg |
| Potato starch | 70 mg |
| Polyvinyl pyrrolidone | 10 mg |
| Magnesium stearate | 5 mg |

The aforesaid cyclopentenone compound obtained in Example 29, lactose and potato starch were mixed, and the mixture was evenly wetted with a 20% ethanol solution of polyvinyl pyrrolidone. The wetted mixture was passed through a sieve. The resulting granules were mixed with magnesium stearate, and compression-molded into tablets.

EXAMPLE 41

Preparation of an Injectable Solution (7E)-7,8-dehydro PGA$_1$ obtained in Example 2 as an active ingredient was dissolved in an amount of 60 μg in 5 ml of ethanol, and the solution was sterilized by passing it through a bacteria-holding filter. 0.1 ml of the solution was filled in each of 1-ml ampoules and the ampoules were sealed up. The contents of the ampoules are diluted, for example, with Tris-HCl buffer to 1 ml for injection.

EXAMPLE 42

Production of a Powder

A powder was prepared in accordance with the following recipe.

| | |
|---|---|
| 4-(1-Octenyl)-5-(6-methoxy-carbonylhexylidene)-2-cyclopentanone | 10 μg |
| Lactose | 100 mg |
| Corn starch | 100 mg |
| Hydroxypropyl cellulose | 10 mg |

The above cyclopentenone compound obtained as a typical active ingredient, lactose and corn starch were mixed, and an aqueous solution of hydroxypropyl cellulose was added. The mixture was dried to form a powder.

What is claimed is:

1. A 5-alkylidene-4-substituted-2-cyclopentenone represented by the following formula (I)-2

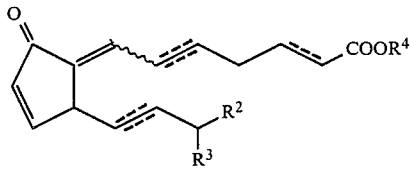

wherein
   R$^2$ represents a hydrogen atom, a linear or branched alkyl group having 1 to 9 carbon atoms which may have a substituent, or a cycloalkyl group having 3 to 8 carbon atoms which may have a substituent;
   R$^3$ represents a hydrogen atom, a hydroxyl group, or a hydroxyl group protected by a tri(C$_{1-7}$ hydrocarbon) silyl group or an acetal linkage togehter with the oxygen atom of the hydroxyl group;
   R$^4$ represents a hydrogen atom, an alkyl group having 1 to 10 carbon atoms or one equivalent of a cation;
   the symbol ≡≡≡≡ represents a single, double or triple bond;
   the symbol ≡≡≡≡ represents a single or double bond; and
   the substitutents are selected from the group consisting of a group of the formula —COOR$^4$ in which R$^4$ is defined as above; a group of the formula —OR$^5$ in which R$^5$ represents a hydrogen atom, an alkyl group having 1 to 6 carbon atoms which may be substituted by a halogen atom, a carbonacyl group having 1 to 7 carbon atoms, or a phenyl group, the phenyl group being optionally substituted by a halogen atom, an alkyl group having 1 to 4 carbon atoms or an alkoxy group having 1 to 4 carbon atoms; a phenyl group which may be substituted by a halogen atom, an alkyl group having 1 to 4 carbon atoms or an alkoxy group having 1 to 4 carbon atoms; and a cycloalkyl group having 3 to 8 carbon atoms which may be substituted by a halogen atom, an alkyl group having 1 to 4 carbon atoms or an alkoxy group having 1 to 4 carbon atoms.

2. A method for inhibiting proliferation of leukemia cells in which the leukemia cells are present in an animal in which the cancer cells are present which comprises administering to said animal an inhibitor dose of 4,5-disubstituted-2-cyclopentenone represented by the following formula (I)-2:

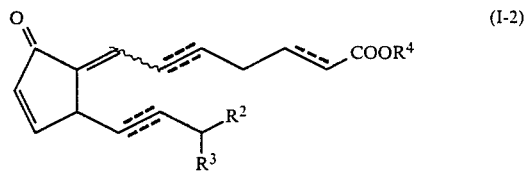

wherein
   R$^2$, R$^3$, R$^4$ and the symbol ≡≡≡≡ are the same as defined below, and the symbol ≡≡≡≡ represents a single or double bond;
   R$^2$ represents a hydrogen atom, a linear or branched alkyl group having 1 to 9 carbon atoms which may have a substituent, or a cycloalkyl group having 3 to 8 carbon atoms which may have a substituent;
   R$^3$ represents a hydrogen atom, a hydroxyl group, or a hydroxyl group protected by a tri(C$_{1-7}$ hydrocarbon) silyl group or an acetyl linkage together with the oxygen atom of the hydroxy group;
   R$^4$ represents a hydrogen atom, an alkyl group having 1 to 10 carbon atoms or 1 equivalent of a cation;
   and said substituents are selected from the group consisting of a group of the formula —COOR$^4$ in which R$^4$ is as defined above, a group of the formula —OR$^5$ in which R$^5$ represents a hydrogen atom, an alkyl group having 1 to 6 carbon atoms which may be substituted by a halogen atom, a carboacyl group having 1 to 7 carbon atoms or a phenyl group, the phenyl group being optionally substituted by a halogen atom, an alkyl group having 1 to 4 carbon atoms or an alkoxy group having 1 to 4 carbon atoms; a phenyl group which may be substituted by a halogen atom, an alkyl group having 1 to 4 carbon atoms or an alkoxy group having 1 to 4 carbon atoms; and a cycloalkyl group having 3 to 8 carbon atoms which may be substituted by halogen atom, an acid group having 1 to 4 carbon atoms or an alkoxy group having 1 to 4 carbon atoms; and the symbol represents a single, double or triple bond.

3. The method of claim 2 wherein the inhibitory dose is in an amount of from about 1 microgram to 100 milligram/kilogram body weight per day.

4. A pharmaceutical composition for treatment of tumors comprising a therapeutically effective amount of a 5-alkylidene-4-substituted-2-cyclopentenone as an antitumor agent represented by the following formula (I)-2

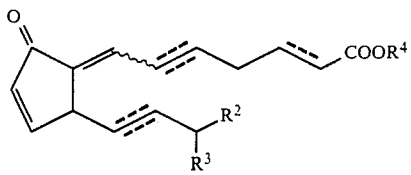 (I-2)

wherein
$R^2$ represents a hydrogen atom, a linear or branched alkyl group having 1 to 9 carbon atoms which may have a substituent, or a cycloalkyl group having 3 to 8 carbon atoms which may have a substituent;
$R^3$ represents a hydrogen atom, a hydroxyl group, or a hydroxyl group protected by a tri($C_{1-7}$ hydrocarbon) silyl group or an acetal linkage together with the oxygen atom of the hydroxyl group;
$R^4$ represents a hydrogen atom, an alkyl group having 1 to 10 carbon atoms or one equivalent of a cation;
the symbol ===== represents a single, double or triple bond;
the symbol ==== represents a single or double bond; and
the substitutents are selected from the group consisting of a group of the formula —$COOR^4$ in which $R^4$ is defined as above; a group of the formula —$OR^5$ in which $R^5$ represents a hydrogen atom, an alkyl group having 1 to 6 carbon atoms which may be substituted by a halogen atom, a carboacyl group having 1 to 7 carbon atoms, or a phenyl group, the phenyl group being optionally substituted by a halogen atom, an alkyl group having 1 to 4 carbon atoms or an alkoxy group having 1 to 4 carbon atoms; a phenyl group which may be substituted by a halogen atom, an alkyl group having 1 to 4 carbon atoms or an alkoxy group having 1 to 4 carbon atoms, and a cycloalkyl group having 3 to 8 carbon atoms which may be substituted by a halogen atom, an alkyl group having 1 to 4 carbon atoms or an alkoxy group having 1 to 4 carbon atoms,
and a pharmaceutically acceptable carrier.

5. A medicament in unit dosage form comprising the pharmaceutical composition of claim 4.

* * * * *

UNITED STATES PATENT AND TRADEMARK OFFICE
CERTIFICATE OF CORRECTION

PATENT NO. : 4,766,147
DATED : August 23, 1988
INVENTOR(S) : RYOJI NOYORI, ET AL.

It is certified that error appears in the above-identified patent and that said Letters Patent is hereby corrected as shown below:

IN THE SPECIFICATION

Column 9, line 11, delete " ------ ", insert -- ------ --.

IN THE CLAIMS

Column 31, line 56; column 32, line 26; column 34, line 1, delete " ------ ", insert -- ------ --.

Column 31, line 63, delete "carbonacyl", insert --carboacyl--.

Column 31, line 68 - column 32, line 1, delete "substittued", insert --substituted--.

Column 32, line 12, delete "inhibitor", insert --inhibitory--.

Signed and Sealed this

Twenty-fourth Day of January, 1989

Attest:

DONALD J. QUIGG

*Attesting Officer*          *Commissioner of Patents and Trademarks*